(12) United States Patent
Babaris

(10) Patent No.: US 11,529,061 B2
(45) Date of Patent: Dec. 20, 2022

(54) SYSTEM AND METHOD FOR MONITORING AND ANALYSIS OF BLOOD PRESSURE

(71) Applicant: JADE HEALTHCARE GROUP INC., Toronto (CA)

(72) Inventor: John Babaris, Toronto (CA)

(73) Assignee: Jade Healthcare Group Inc., Toronto (CA)

( * ) Notice: Subject to any disclaimer, the term of this patent is extended or adjusted under 35 U.S.C. 154(b) by 77 days.

(21) Appl. No.: 16/622,660

(22) PCT Filed: May 31, 2018

(86) PCT No.: PCT/IB2018/053924
§ 371 (c)(1),
(2) Date: Dec. 13, 2019

(87) PCT Pub. No.: WO2018/229587
PCT Pub. Date: Dec. 20, 2018

(65) Prior Publication Data
US 2021/0022626 A1    Jan. 28, 2021

Related U.S. Application Data

(60) Provisional application No. 62/519,914, filed on Jun. 15, 2017.

(51) Int. Cl.
*A61B 5/021* (2006.01)
*A61B 5/00* (2006.01)
*A61B 5/022* (2006.01)

(52) U.S. Cl.
CPC .......... *A61B 5/02141* (2013.01); *A61B 5/002* (2013.01); *A61B 5/022* (2013.01);
(Continued)

(58) Field of Classification Search
CPC . A61B 5/02141; A61B 5/022; A61B 5/02225; A61B 5/02233; A61B 5/681;
(Continued)

(56) References Cited

U.S. PATENT DOCUMENTS 6,808,496 B2    10/2004  Oka et al.
2003/0199773 A1 * 10/2003  Narimatsu ......... A61B 5/02007
                                                            600/490
(Continued)

OTHER PUBLICATIONS

Gilbert, Jean, "International Search Report", International Application No. PCT/IB2018/053924, dated Oct. 31, 2018, 5 pages.
(Continued)

*Primary Examiner* — Sean P Dougherty
*Assistant Examiner* — Kyle W. Kretzer

(57) ABSTRACT

What is disclosed is a system for measurement and analysis of blood pressure of a test subject comprising a blood pressure measuring cuff unit; a waveform analysis subsystem coupled to said blood pressure measuring cuff unit via a network; and wherein said cuff unit acquires a digital pulse pressure waveform from a wrist of the test subject, said digital pulse pressure waveform is transmitted over said network to said waveform analysis subsystem, and said waveform analysis subsystem processes said digital pulse pressure waveform to extract one or more blood pressure parameters and hemodynamic parameters.

14 Claims, 13 Drawing Sheets

(52) U.S. Cl.
CPC ...... *A61B 5/02225* (2013.01); *A61B 5/02233* (2013.01); *A61B 5/681* (2013.01); *A61B 5/7246* (2013.01); *A61B 5/7267* (2013.01); *A61B 5/6824* (2013.01); *A61B 2562/0219* (2013.01)

(58) Field of Classification Search
CPC . A61B 5/6824; A61B 2562/0219; A61B 5/02; A61B 5/021; G16H 50/30; G16H 20/00; G16H 40/67; G16H 50/20; G16H 50/70
See application file for complete search history.

(56) References Cited

U.S. PATENT DOCUMENTS

| | | | |
|---|---|---|---|
| 2004/0193064 A1 | 9/2004 | Shusterman | |
| 2005/0131308 A1 | 6/2005 | Chio et al. | |
| 2007/0106162 A1* | 5/2007 | Illyes | A61B 5/02007 600/481 |
| 2009/0156946 A1* | 6/2009 | Lane | A61B 5/02225 600/490 |
| 2010/0081944 A1* | 4/2010 | Baker, Jr. | A61B 5/02125 600/485 |
| 2012/0330112 A1* | 12/2012 | Lamego | A61B 5/02225 600/301 |
| 2013/0271350 A1* | 10/2013 | Lyons | G06F 1/1641 345/1.1 |
| 2013/0274620 A1* | 10/2013 | Zhang | A61B 5/02125 600/490 |
| 2013/0345576 A1* | 12/2013 | Chen | A61B 5/02225 600/490 |
| 2015/0182147 A1* | 7/2015 | Sato | A61B 5/1079 600/493 |
| 2016/0089042 A1 | 3/2016 | Saponas et al. | |
| 2017/0245769 A1* | 8/2017 | Niehaus | A61B 5/0004 |
| 2017/0367649 A1* | 12/2017 | Kitagawa | A61B 5/02233 |
| 2018/0200140 A1* | 7/2018 | Ganske | G16H 40/40 |

OTHER PUBLICATIONS

Gilbert, Jean, "Written Opinion", International Application No. PCT/IB2018/053924, dated Oct. 31, 2018, 9 pages.

* cited by examiner

SYSTEM AND METHOD FOR MONITORING AND ANALYSIS OF BLOOD PRESSURE

FIELD OF THE INVENTION

The present disclosure relates to monitoring and analysis of blood pressure.

SUMMARY

A system for measurement and analysis of blood pressure of a test subject comprising a blood pressure measuring cuff unit; a waveform analysis subsystem coupled to said blood pressure measuring cuff unit via a network; and wherein said cuff unit acquires a digital pulse pressure waveform from a wrist of the test subject, said digital pulse pressure waveform is transmitted over said network to said waveform analysis subsystem, and said waveform analysis subsystem processes said digital pulse pressure waveform to extract one or more blood pressure parameters and hemodynamic parameters.

A system for measurement and analysis of blood pressure of a plurality of test subjects, said system comprising a blood pressure measuring cuff unit; a waveform analysis subsystem coupled to said blood pressure measuring cuff via a network; and wherein said cuff unit acquires a plurality of digital pulse pressure waveforms, wherein each of said plurality of digital pulse pressure waveforms is obtained from a wrist of each of the plurality of test subjects, said plurality of digital pulse pressure waveforms are transmitted over said network to said waveform analysis subsystem, and said waveform analysis subsystem processes said plurality of digital pulse pressure waveform to extract blood pressure parameters and hemodynamic parameters corresponding to each of said plurality of test subjects.

A method for measuring and analyzing blood pressure of a test subject, said method comprising acquiring a digital pulse pressure waveform from a wrist of the test subject; transmitting the acquired digital pulse pressure waveform over a network; processing said transmitted digital pulse pressure waveform; extracting, based on said processing, one or more blood pressure parameters and hemodynamic parameters.

A method of assembling a cuff unit comprising one or more components for blood pressure measurement and analysis of a test subject, comprising constructing said cuff unit using a plurality of modules, said constructing comprising distributing some of said one or more components within said plurality of modules, and arranging said plurality of modules adjacent to each other to enable said cuff unit to wrap around a wrist of the test subject.

A method for measurement and analysis of blood pressure of a plurality of test subjects, said method comprising acquiring each of a plurality of digital pulse pressure waveforms from a wrist of each of the plurality of test subjects; transmitting the plurality of digital pulse pressure waveforms over a network; processing said transmitted plurality of digital pulse pressure waveforms; extracting, based on said processing, one or more blood pressure parameters and hemodynamic parameters.

The foregoing and additional aspects and embodiments of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the disclosure will become apparent upon reading the following detailed description and upon reference to the drawings.

FIG. 2I shows an example construction of a cuff unit.

Figure 1:
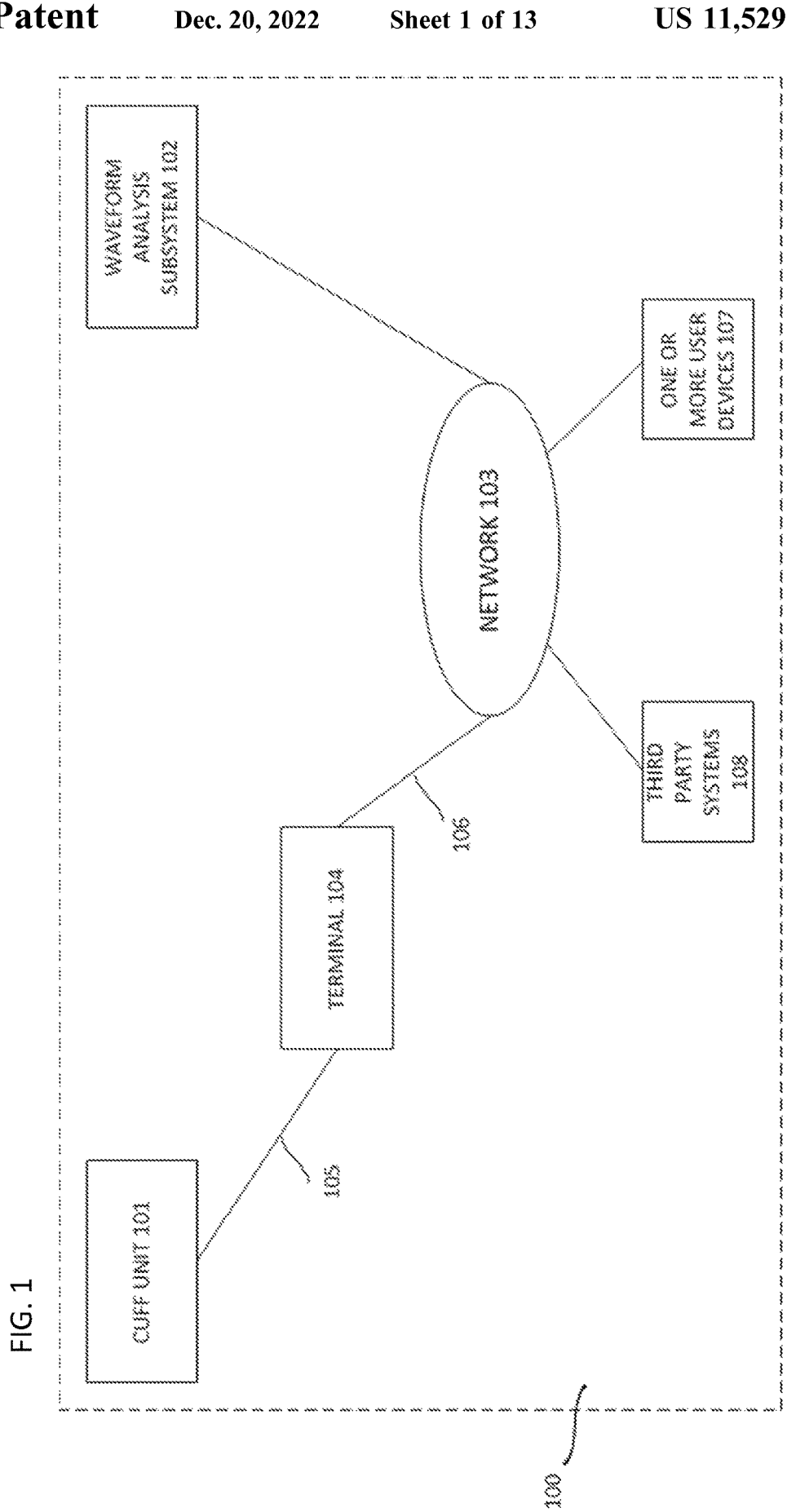
FIG. 1 shows an example embodiment of a system for blood pressure measurement and analysis.

While the present disclosure is susceptible to various modifications and alternative forms, specific embodiments or implementations have been shown by way of example in the drawings and will be described in detail herein. It should be understood, however, that the disclosure is not intended to be limited to the particular forms disclosed. Rather, the disclosure is to cover all modifications, equivalents, and alternatives falling within the spirit and scope of an invention as defined by the appended claims.

DETAILED DESCRIPTION

The following details a system and method for wrist-based oscillometric blood pressure measurement and analysis.

Wrist-based systems enjoy several advantages over arm-based systems. Firstly, the raw pulse pressure waveforms used to obtain radial arterial waveforms and results such as the radial augmentation index (RAI) are obtained at the radial artery on the wrist, not at the arm. This is because better quality results are obtained from measurements on the radial artery versus measurements from the arm. For example, in "Cuff Pressure Pulse Waveforms: Their Current and Prospective Application in Biomedical Instrumentation" by Stork, Milan, and Jiri Jilek in Biomedical Engineering, Trends in Electronics, Communication and Software: pages 193-210; it was shown that waveforms obtained from the wrist have more sharply defined contours when compared the waveforms obtained from the arm. Furthermore, if designed properly, wrist monitors are generally easier to fasten than arm monitors. For a home-based consumer this improves usability and accuracy of measurement. For most people, wrist-based systems offer less discomfort than arm-based systems as squeezing the upper arm is more painful than squeezing the wrist. This also improves usability for a home-based consumer. With a wrist-based monitor it is much less likely that a user will have to remove clothing before fastening the cuff. For home-based consumers this increases ease of use, reduces frustrations and is likely to improve compliance with regular testing regimes. Wrist-based monitors usually take up less space and are therefore more portable than arm-based monitors, which encourages users to keep it with them throughout the day. For a home-based consumer this is likely to improve compliance with regular testing regimes. Finally, there is lower variability in wrist sizes as compared to arm sizes. This reduces the risk of using a wrongly-sized cuff and therefore measurement errors.

However wrist-based systems have several shortcomings when compared to arm based systems. For example, wrist-based systems have a higher risk of limbs being incorrectly positioned during measurement. This leads to a higher risk of measurement error. Many wrist-based systems which use cuffs also have a risk of incorrect cuff orientation. This is typically because the bladder which inflates during testing does not wrap around the wrist fully and therefore incorrect positioning of the bladder can affect results obtained. Signals from wrist-based systems are more complex, dynamic and susceptible to user movement and therefore require a higher level of processing and quality control. While wrist-based monitors usually are smaller than arm-based monitors, many prior art systems often house all the components in a bulky package on the wrist, thereby partially negating some of the size advantages offered by wrist-based monitors.

Typically, applanation tonometry (AT) is used at the wrist to obtain radial arterial waveforms and results such as the radial augmentation index (RAI). However, oscillometric systems enjoy several advantages over AT systems. In Jílek, Jiṕ, and Milan πtork. "A wrist cuff method for acquisition and analysis of radial artery waveforms used for blood pressure measuring." (2007); it was explained that skilled application of a tonometer is necessary in order to acquire correct waveforms, and that errors have been reported. Thus, to reduce errors, usually only trained personnel are allowed to use an AT system. This increases costs and reduces accessibility to the system for home-based consumers. As was shown in Jílek, Jiṕ, and Milan πtork. "A wrist cuff method for acquisition and analysis of radial artery waveforms used for blood pressure measuring." (2007) and Stork, Milan, and Jiri Jilek. "Cuff Pressure Pulse Waveforms: Their Current and Prospective Application in Biomedical Instrumentation." Biomedical Engineering, Trends in Electronics, Communication and Software: 193-210; waveforms obtained via oscillometric methods and AT methods show very similar features.

Furthermore, the equipment necessary to perform AT measurements is relatively expensive when compared to the cost of oscillometric waveform measuring equipment. This further increases the cost of performing AT measurements, and therefore reduces accessibility to home-based consumers. On the other hand, most home blood pressure monitors are based on oscillometric waveform measurement.

The system and method detailed below maintains the advantages of wrist-based systems over arm-based systems while overcoming the shortcomings of wrist-based systems compared to arm-based systems. In addition, since the system and method detailed below is oscillometric-based, it enjoys several advantages over AT systems as described above.

FIG. 1 shows one embodiment of the system below. As shown in FIG. 1, in system 100, blood pressure measuring cuff unit 101 is coupled to the waveform analysis subsystem 102 via network 103, terminal 104 and connections 105 and 106. Other coupling arrangements are also possible. For example, in some embodiments, cuff unit 101 is coupled to waveform analysis subsystem 102 via network 103 without coupling to terminal 104. Users of system 100 include, for example, hospitals, clinics, nurses, doctors, home-based consumers, medical equipment corporations and research institutions.

Figure 2:
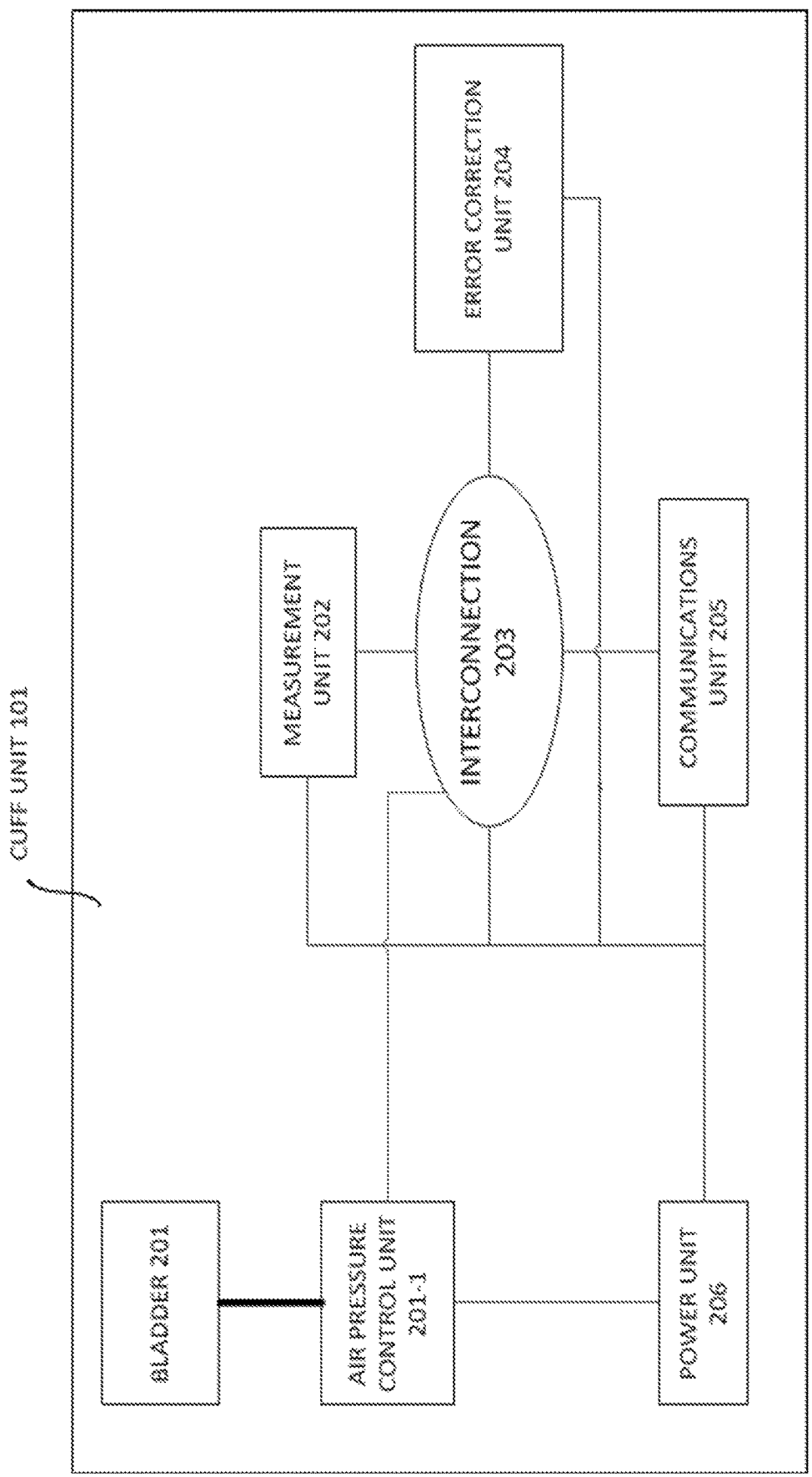
FIG. 2 shows an example embodiment of a blood pressure measuring cuff unit.

Blood pressure measuring cuff unit 101 is designed for application to a wrist of a person who is a test subject, so as to perform tests to acquire signals using an oscillometric technique. The test subject is, for example, a patient in a doctor's clinic or a hospital, a participant in a researcher's study, or a home-based consumer. The test is, for example, self-administered by the test subject, or a practitioner or a researcher. FIG. 2 shows a detailed diagram of the blood pressure measuring cuff unit 101. In one embodiment, cuff unit 101 comprises bladder 201, air pressure control unit 201-1, measurement unit 202, error correction unit 204, communications unit 205, power unit 206 and interconnection 203.

Bladder 201 is inflatable. The material used to make the bladder 201 is air tight and be flexible enough to allow the bladder 201 to conform to the shape of the test subject's wrist. Bladder 201 is controlled by air pressure control unit 201-1. Air pressure control unit 201-1 comprises one or more valves to allow the ingress and egress of air to the bladder 201 so as to inflate and deflate the bladder 201. Additionally, air pressure control unit 201-1 comprises a pump for inflation of bladder 201. In a further embodiment, the one or more valves in air pressure control unit 201-1 comprises a fast release valve which allows for a fast deflation of the bladder 201; and a slow release valve or a 'leak valve_ which allows for a controlled deflation of the bladder 201. In some embodiments, the bladder 201 is capable of inflating to a peak pressure of 350 mmHg.

In one embodiment, bladder 201 wraps around the wrist of a test subject. This enables substantially similar measurements, such as digital pulse pressure waveforms, to be obtained by cuff unit 101 irrespective of the orientation of the cuff unit 101 during attachment to the wrist. Specifically, the obtained digital pulse pressure waveforms are substantially invariant with respect to an angle of rotation of cuff unit 101 during attachment to the wrist. Then, substantially similar digital pulse pressure waveforms are obtained over the possible 360 degree range of angles of rotation.

Figure 2B:
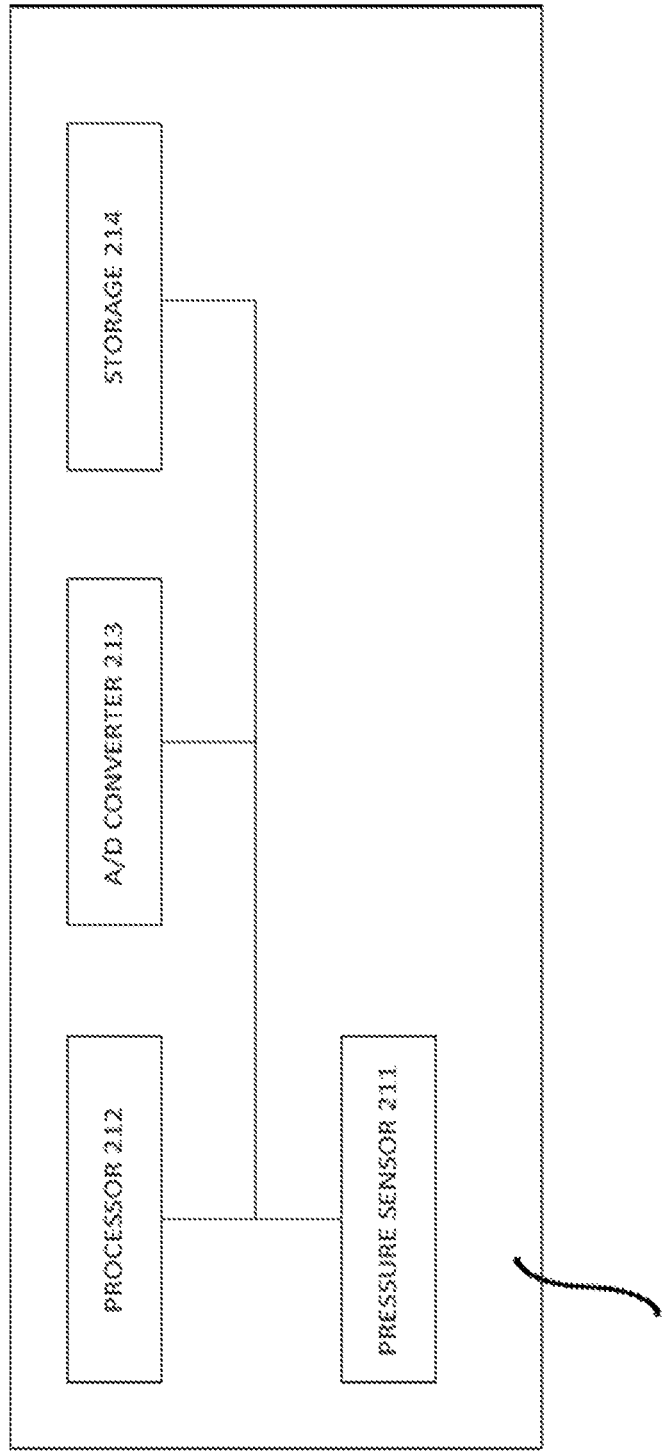
FIG. 2B shows an example embodiment of a measurement unit within a blood pressure measuring cuff unit.

Measurement unit 202 controls the operation of cuff 101. FIG. 2B shows a detailed diagram of measurement unit 202. As shown in FIG. 2B, measurement unit 202 comprises pressure sensor 211. Measurement unit 202 also comprises processor 212, analog-to-digital (A/D) converter 213 and digital storage 214 which are all electrically connected to each other. Processor 212 controls the operation of measurement unit 202 by implementing algorithms necessary to ensure readings of pulse pressure waveforms from a test subject's wrist. Processor 212 also handles all communications between measurement unit 202 and the other components of the cuff unit 101.

A/D converter 213 samples the analog pulse pressure waveform captured by pressure sensor 211 at an appropriate sampling frequency, and then converts the sampled waveform into a digital pulse pressure waveform. In some embodiments, A/D converter 213 has a 24-bit or higher resolution. As will be explained later, having a 24-bit or higher resolution offers certain advantages for the operation of system 100.

Storage 214 is used to store data temporarily after conversion by A/D converter 213. In addition storage 214 may store other data received from other components of measurement unit 202 such as error correction unit 204.

In addition, cuff unit 101 comprises an error correction unit 204. The error correction system acts to provide readings necessary to, for example, correct for at least one of incorrect limb positioning and limb movements made by the test subject. In one embodiment, error correction system 204 is a 3-axis accelerometer. In a further embodiment, data recorded by error correction system 204 is supplied to measurement unit 202 so as to be included with digital pulse pressure waveforms. In another embodiment, error correction unit 204 is part of measurement unit 202.

Cuff unit 101 also comprises communication unit 205. This unit is responsible for receiving data and commands from, and transmitting data and commands to, for example, terminal 104. In one embodiment, communication unit 205 comprises specialized processors to enable the operation of various communication protocols. For example, in the embodiments where cuff unit 101 connects to terminal 104 via personal area networking technologies such as Bluetooth or Zigbee, communication unit 205 readily facilitates communications using either of these protocols. In the embodiments where cuff unit 101 connects to network 103 directly, communication unit 205 facilitates communications using protocols such as Wi-Fi, Global System for Mobile communications (GSM), Long-Term Evolution (LTE), WiMax, Code Division Multiple Access (CDMA)

As shown in FIG. 2, power unit 206 is coupled to the other components of cuff unit 101 via so as to supply power to these components. In some embodiments, power unit 206 comprises an alternating current (AC) adapter for connection to a mains supply. In some embodiments, power unit 206 comprises one or more batteries. In some embodiments, the one or more batteries comprise a rechargeable battery. In embodiments where power unit 206 is a rechargeable battery, power unit 206 is charged using:

wired charging techniques known to those of skill in the art; or wireless charging techniques known to those of skill in the art, such as the Qi protocol.

In further embodiments, power unit 206 comprises one or more batteries and an AC adapter. Then, if power unit 206 is not connected to a mains supply, cuff unit 101 is powered by the one or more batteries. However, if power unit 206 is connected to a mains supply then the cuff unit 101 stops being powered by the one or more batteries. In some of the embodiments where the one or more batteries comprises a rechargeable battery, when power unit 206 is connected to a mains supply the rechargeable battery is then charged.

Interconnection 203 electrically couples the components of cuff unit 101 together. In some embodiments, interconnection 203 is a flexible backplane. In other embodiments, interconnection 203 is comprised of one or more cables within the cuff unit 101.

Figure 2C:
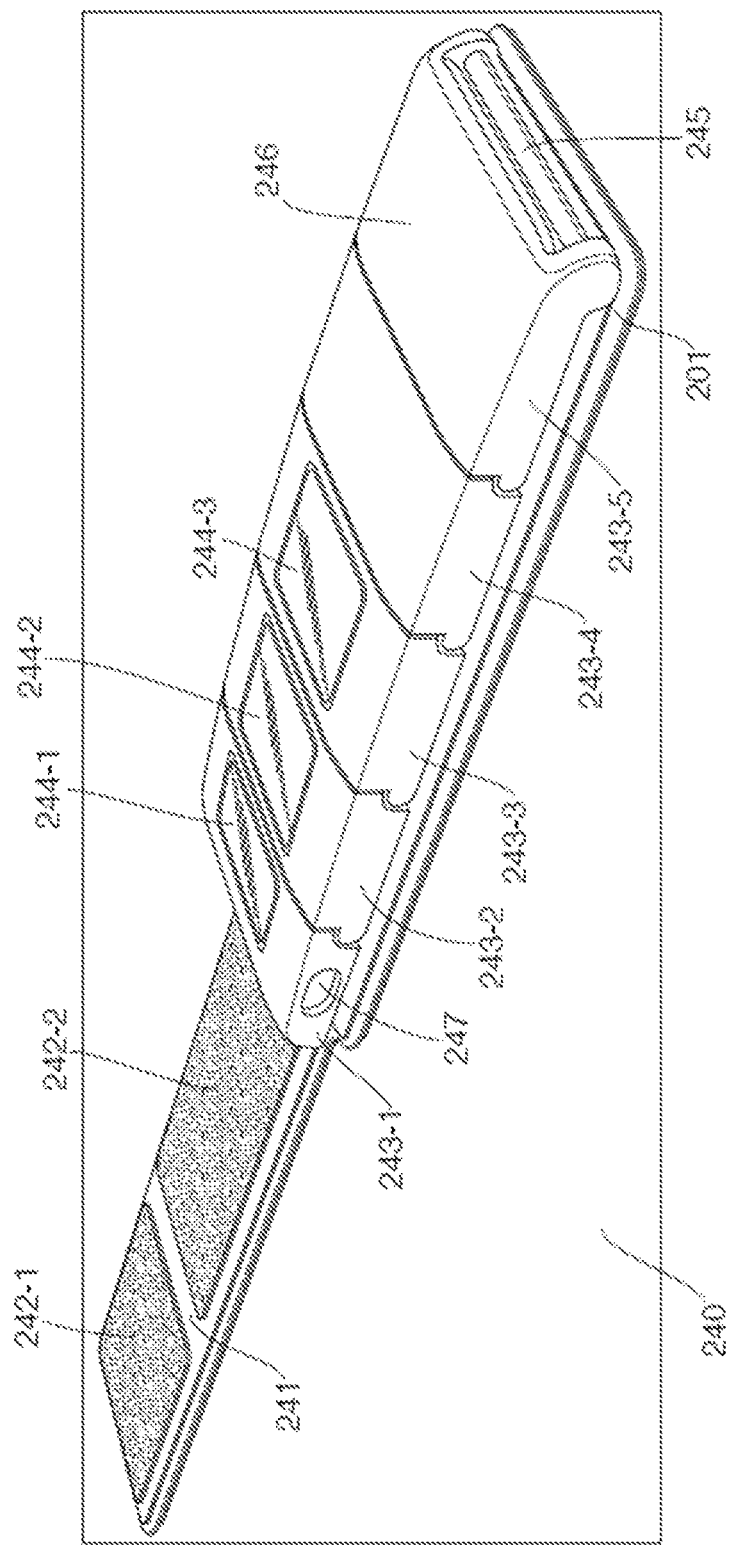
FIG. 2C shows an example embodiment of a form factor for a blood pressure measuring cuff unit in unfastened mode.

In one embodiment, cuff unit 101 has a form factor 240 as shown in FIG. 2C. In FIG. 2C, form factor 240 comprises a housing 246, strap 241 and bladder 201. In FIG. 2C, form factor 240 is in unfastened mode, that is, when it is not strapped or fastened on the wrist of a test subject. Form factor 240 is a modular form factor, as housing 246 comprises modules 243-1 to 243-5.

In an embodiment, some of the components of the cuff unit 101 are distributed within modules 243-1 to 243-5. In some embodiments, different parts of each of the components are distributed within modules 243-1 to 243-5.

An example embodiment is described below: As previously described above, air pressure control unit 201-1 comprises a pump and one or more valves. Then, an example distribution is as follows:

243-1: All subcomponents of measurement unit 202 except for pressure sensor 211 and A/D converter 213, error correction unit 204 and communications unit 205;

243-2: The one or more valves which are part of air pressure control unit 201-1;

243-3: Power unit 206;

243-4: The pump which is part of air pressure control unit 201-1; and 243-5: Pressure sensor 211 and A/D converter 213.

As shown in FIG. 2C, modules 243-1 to 243-5 are connected to each other by hinges. This allows each module the ability to move independently and the entirety of form factor 240 to wrap around a test subject's wrist, as will be further described below. Then, interconnection 203 connects any subcomponents or components residing within each module to the other subcomponents or components residing in the other modules via the hinges.

As shown in FIG. 2C bladder 201 is made to wrap around a test subject's wrist. This ensures that digital pulse pressure waveforms acquired by cuff unit 101 are substantially invariant over different rotation angles when attached to a test subject's wrist. Housing 246 further comprises programmable power button switch 247 with a programmable indication light which turns on whenever cuff unit 101 is in use. In one embodiment, this light is a Light Emitting Diode (LED). Housing 246 also comprises pads 244-1, 244-2 and 244-3; and pin 245. These components of housing 246 are used for fastening cuff 101, as will be detailed below.

Strap 241 is also used to fasten cuff unit 101 on the wrist of a test subject. Strap 241 comprises pads 242-1 and 242-2. These are made to attach to pads 244-1, 244-2 and 244-3; which will be described in further detail below. In one embodiment pads 242-1, 242-2, 244-1, 244-2 and 244-3 are constructed using a hook and loop fabric such as VEL-CRO®, as would be known to one of skill in the art.

In another embodiment, the fastening of cuff unit 101 is performed using a magnetic latch system.

Figure 2D:
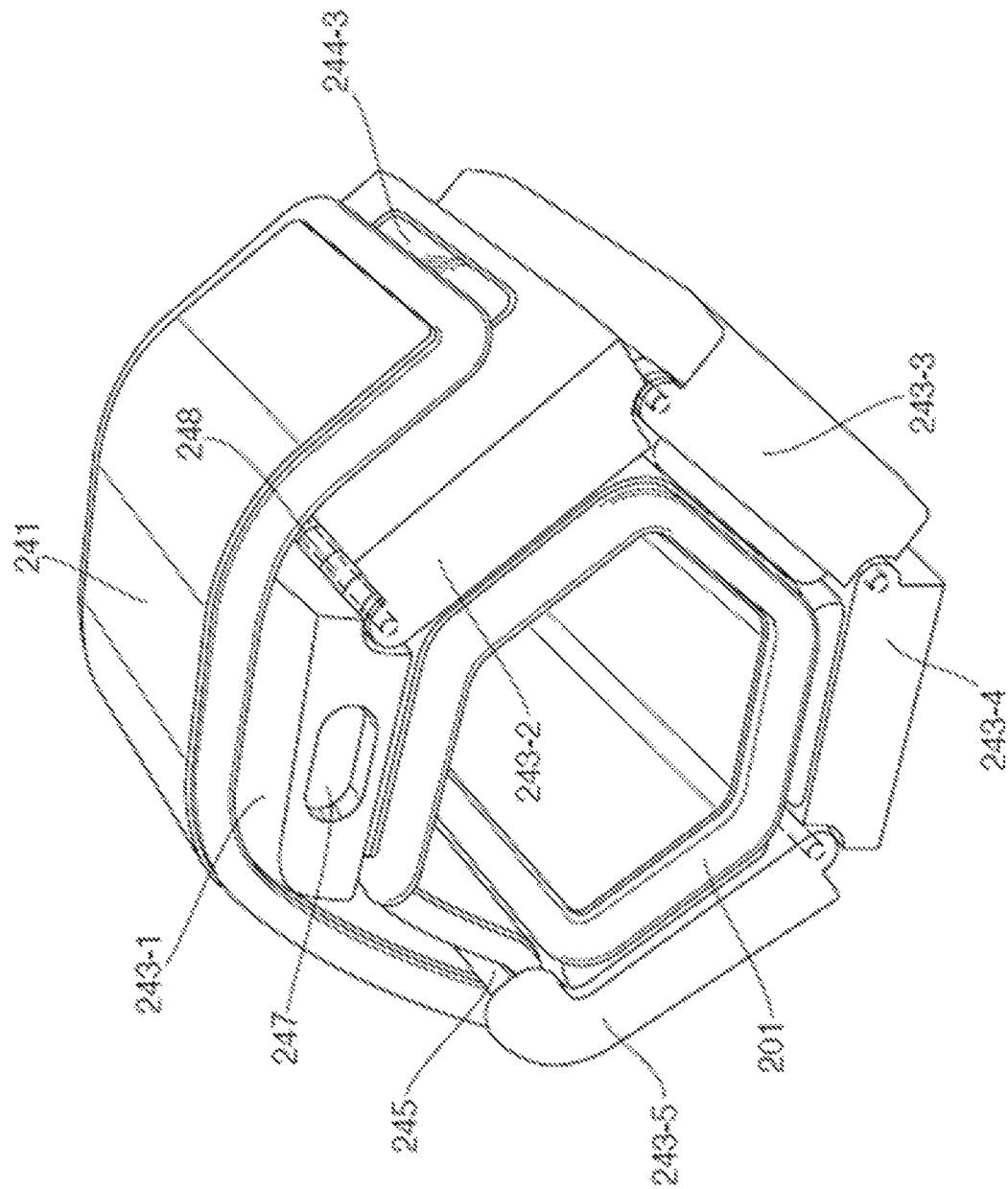
FIG. 2D shows an example embodiment of a form factor for a blood pressure measuring cuff unit in fastened mode.
Figure 2E:
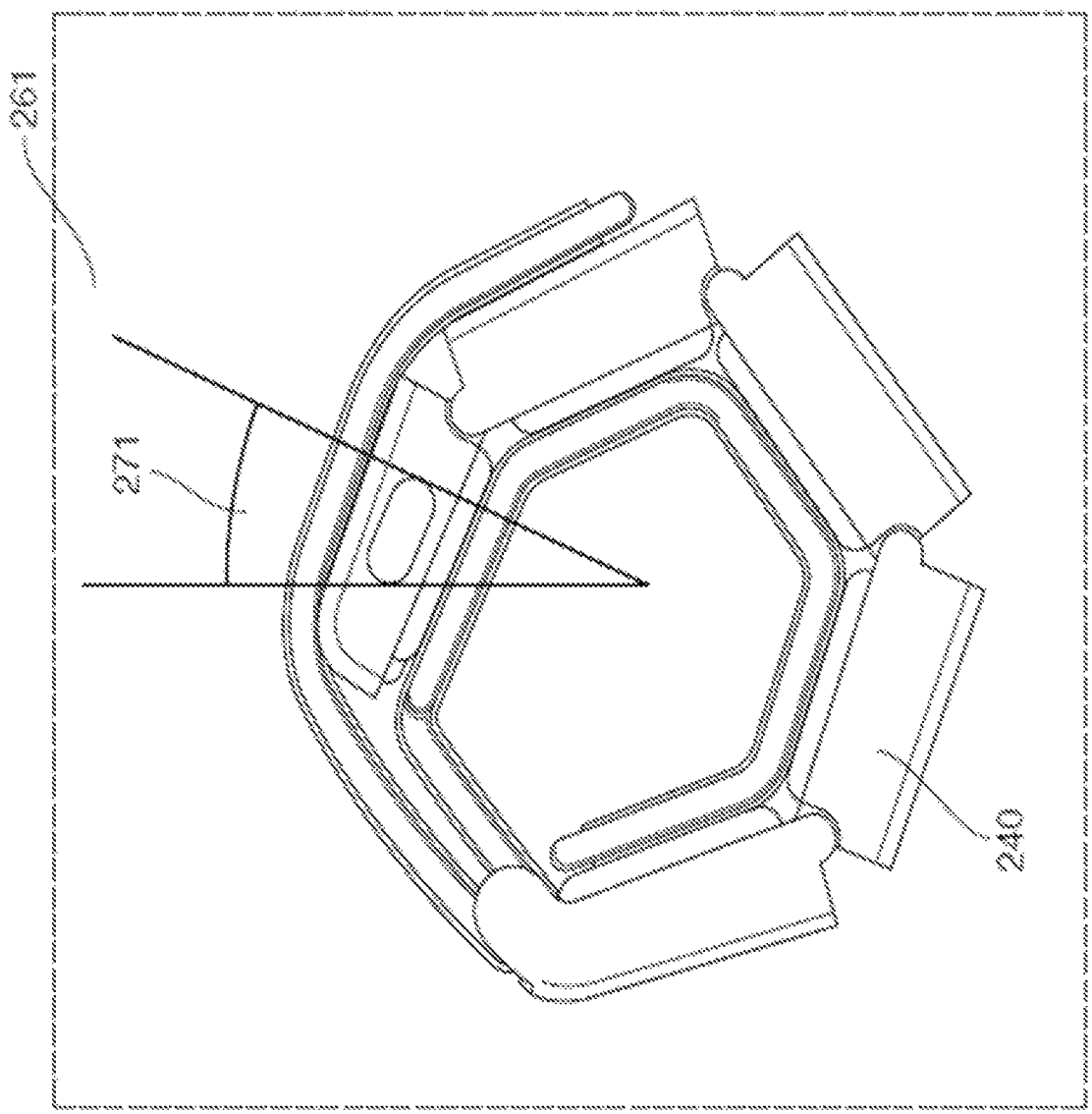
FIGS. 2E to 2H show four different orientations of a form factor when attached to the wrist of a test subject.
Figure 2F:
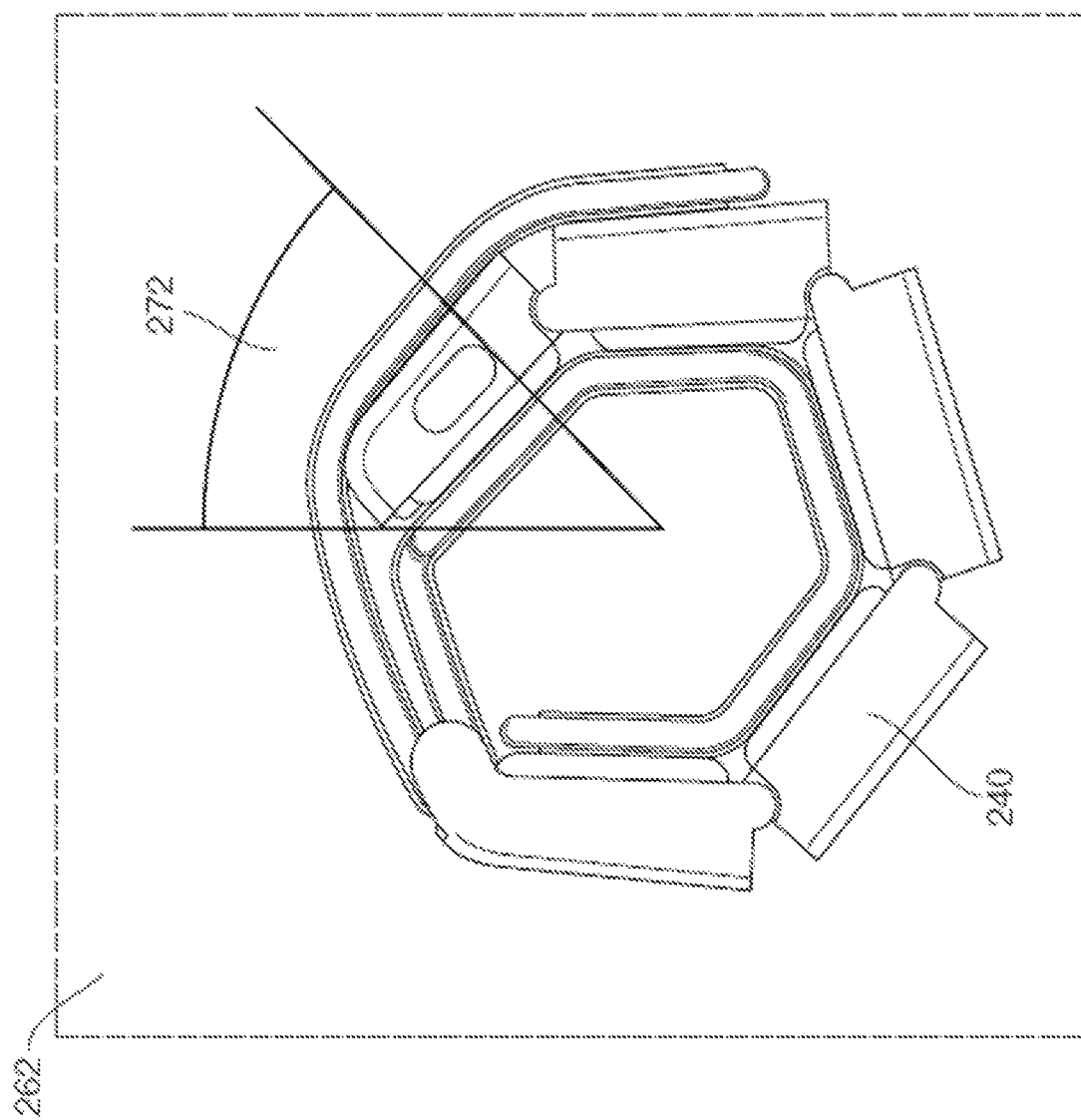
Figure 2G:
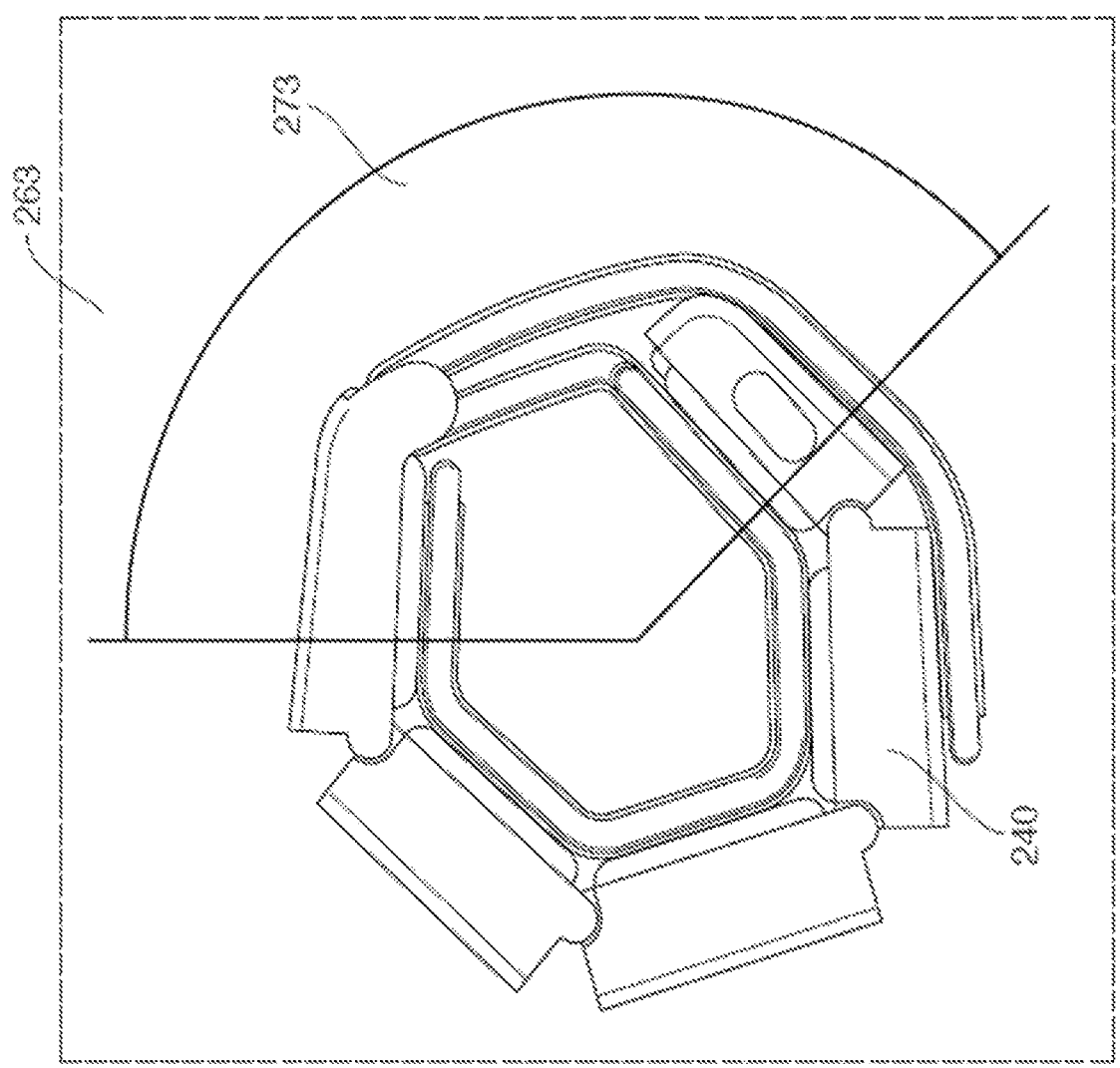
Figure 2H:
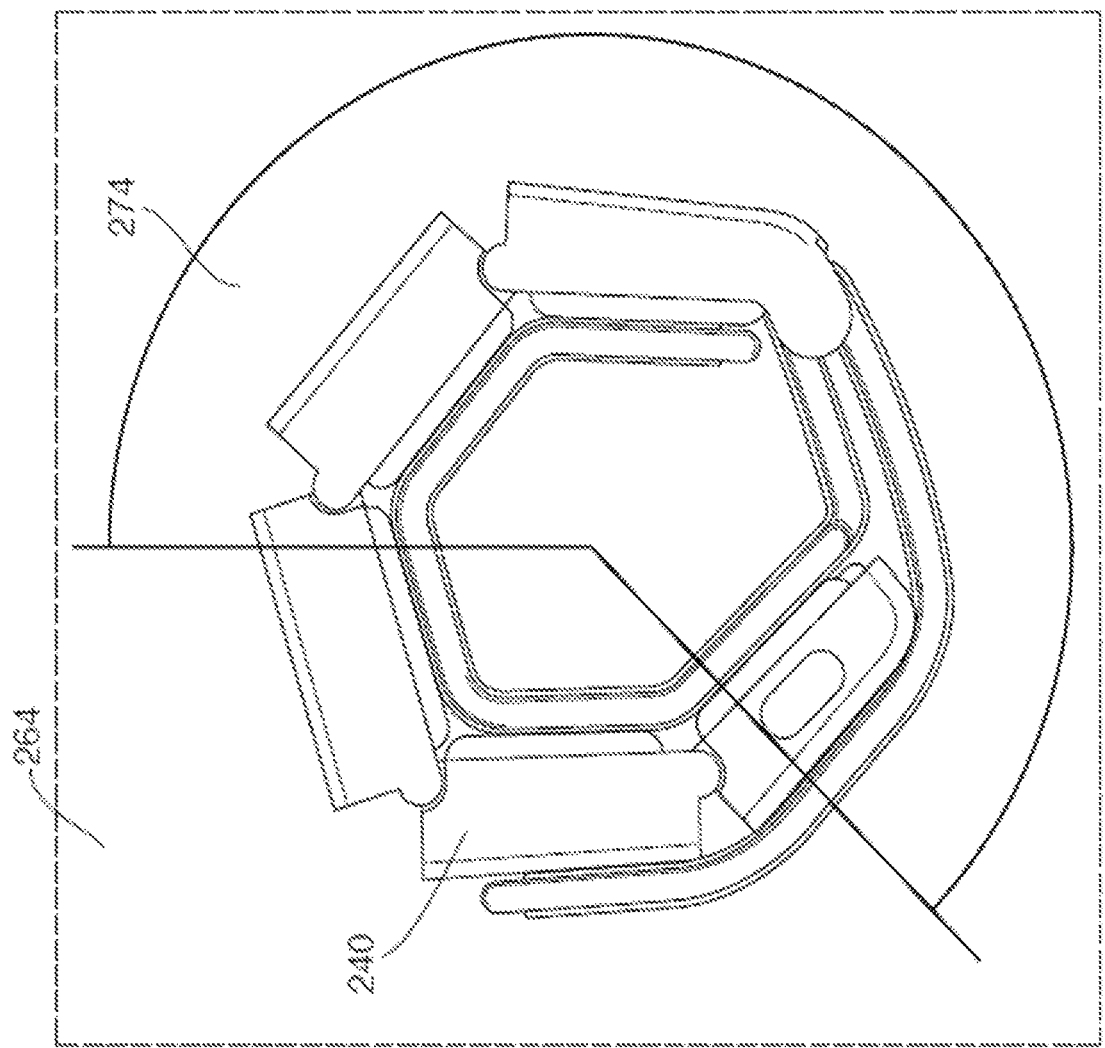
Figure 21:
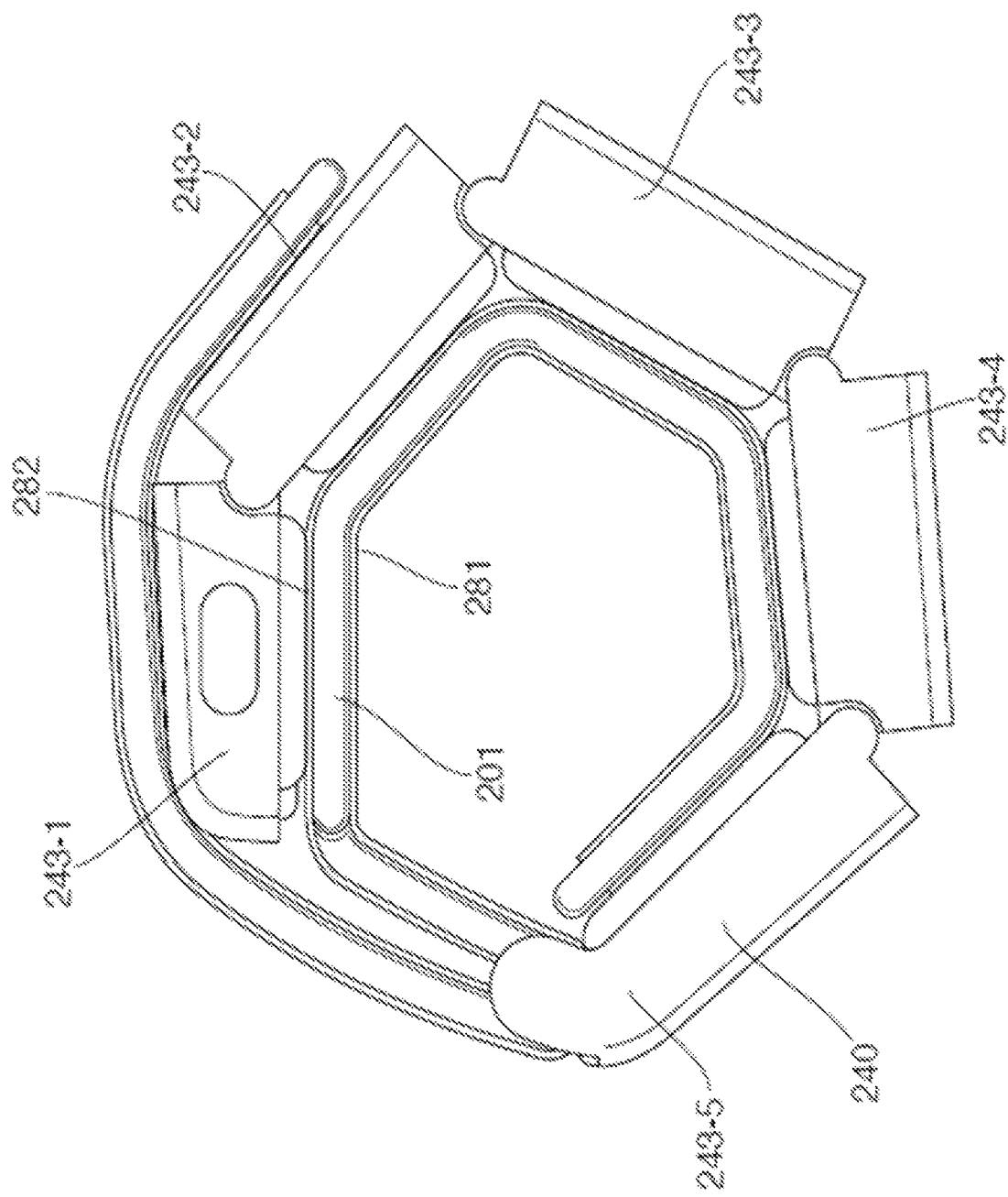

FIG. 2D shows form factor 240 in fastened mode; that is, when it is strapped or fastened on the wrist of a test subject. As can be seen in FIG. 2D, the modules 243-1 to 243-5 are hinged, as exemplified by hinge 248 connecting module 243-1 to 243-2. This allows each module to move independently so as to ensure a tight fit around the wrist of a test subject. As is shown in FIG. 2D, strap 241 wraps around pin 245 and when pulled tight, allows for a tight fit around the wrist of a test subject. Then, pads 242-1 and 242-2 attach to pads 244-1, 244-2 and 244-3 so as to securely fasten cuff 101 to the wrist of a test subject.

As shown in FIG. 2D, bladder 201 wraps around the wrist when form factor 240 is in fastened mode. As explained previously, this enables the digital pulse pressure waveforms obtained by cuff unit 101 to be substantially invariant over the possible 360 degree range of angles of rotation.

This is described further as follows: FIGS. 2E-2H show four example orientations 261-264 of the form factor 240 in fastened mode. Each of these orientations corresponds to four example angles of rotation 271-274. Substantially similar digital pulse pressure waveforms are obtained for these four orientations, wherein each orientation comprises a different angle of rotation.

Care has to be taken with the construction of the cuff to ensure that when bladder 201 inflates and deflates, interconnection 203 between modules 243-1 to 243-5 is preserved and the cuff unit 101 continues to operate in a stable manner.

An example construction to achieve this is explained in further detail below with reference to FIG. 2I. In FIG. 2I, the bladder 201 resides between inner layer 281 and outer layer 282. The inner layer 281 is in contact with the wrist of a test subject. The material used to make inner layer 281 has high material elasticity so as to enable high flexibility. This allows the inner layer 281 to expand when the bladder 201 inflates. An example of such a material is a very light weight spandex. As shown in FIG. 2I modules 243-1 to 243-5 are attached to outer layer 282. The material used to make outer layer 282 has low material elasticity and therefore low flexibility in order to contain the pressure applied to the wrist. This assists in maintaining stable operation of the modules 243-1 to 243-5.

Form factor 240 has several advantages. By using a modular design such as demonstrated in FIGS. 2C and 2D, the following is achieved:

cuff unit 101 will follow the curvature of the wrist of the test subject, so as to wrap securely around the wrist of the test subject, and the components of cuff unit 101 are distributed along the length of the bladder 201, thereby reducing the thickness of cuff unit 101 compared to the prior art wrist based systems. In one embodiment, the thickness of the cuff unit is limited to a maximum of 15 mm (0.59 inches). This reduction and limiting serve to enhance the portability of the cuff unit. Increased portability improves the likelihood of compliance of a test subject with testing regimes.

In one embodiment, the size of each of the modules 243-1 to 243-5 is set to fall within an optimal range due to the following: Each of the modules 243-1 to 243-5 need to accommodate at least some part of each of the components which are distributed within modules 243-1 to 243-5. For example, each of the modules need to accommodate at least one subcomponent of each of the components which are distributed within modules 243-1 to 243-5. Therefore the modules have to be large enough to be able to fulfil this requirement. However, if the modules are too large, this makes it difficult for the bladder 201 and therefore the cuff unit 101 to wrap securely around various sized wrists of the various test subjects. Therefore, the modules are optimized to fall within a size range so as to meet these constraints. This optimization further enhances the advantages of the form factor 240 as described above.

While the above demonstrates exemplary embodiments of cuff unit 101, one of skill in the art would readily appreciate that other embodiments are also possible. In a further embodiment, cuff unit 101 comprises a display. This display is, for example, an external display connected to cuff unit 101. This connection is achieved using, for example, a Universal Serial Bus (USB) connection. In another embodiment, the display is a flexible display which is integrated within form factor 240. In a further embodiment, cuff unit 101 comprises a touchscreen. In one embodiment, the touchscreen is bendable or flexible so as to allow integration within form factor 240. An example of a touchscreen or flexible display can be found in, for example, http://www.cambridgesciencepark.co.uk/flexenable-named-one-2016s-top-innovators/, retrieved Jun. 11, 2017 and attached in Appendix A. In another embodiment, the touchscreen is external to cuff unit 101 and connected to cuff unit 101 via, for example, a USB connection.

Other form factors are also possible. For example, in one embodiment, instead of hinged modules 243-1 to 243-5, a flexible band is used. This flexible band is attached to, for example, bladder 201. Then, measurement unit 202, error correction unit 204 and communications unit 205 are distributed around the band and interconnection 203 is a flexible backplane. Such a design has the advantage of allowing easier integration of a flexible display or a touchscreen with cuff unit 101.

Figure 2J:
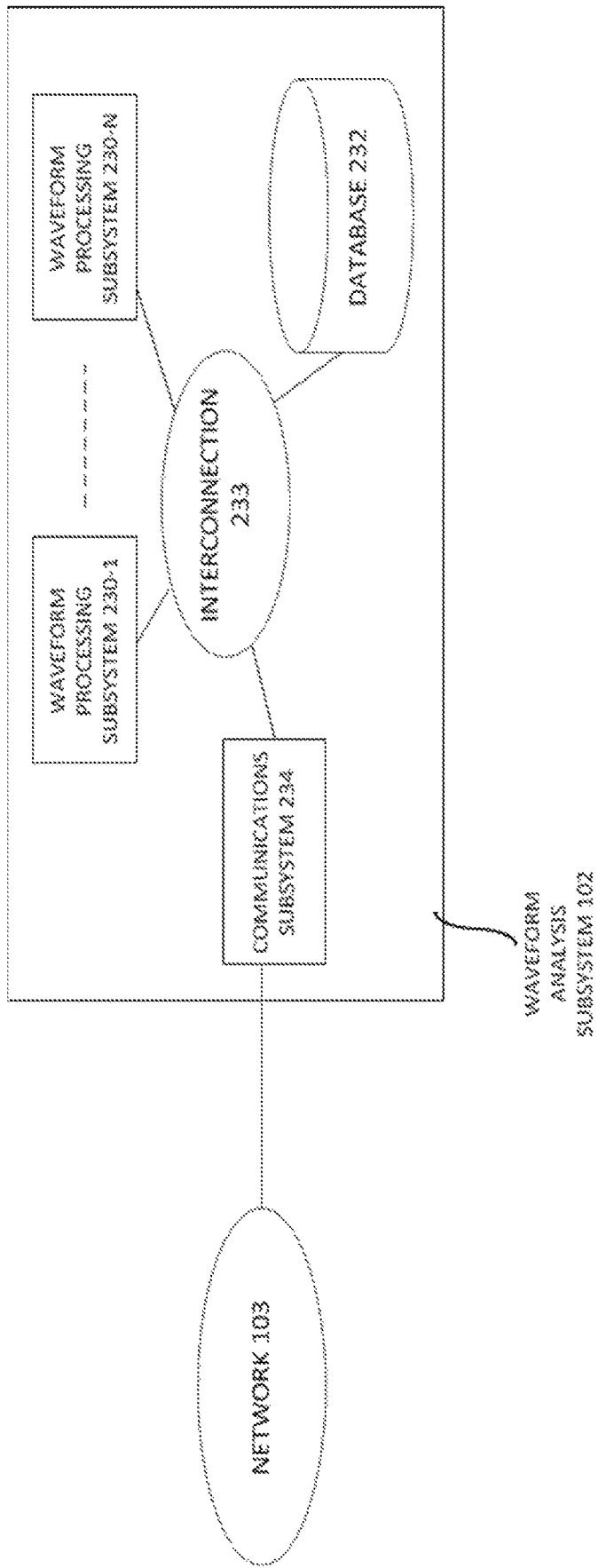
FIG. 2J shows an example embodiment of a waveform analysis subsystem.

Waveform analysis subsystem 102 performs analysis of waveforms captured by cuff unit 101 as well as other processing and calculations within system 100 as necessary. Waveform analysis subsystem 102 is described in more detail in FIG. 2J. In FIG. 2J, communications subsystem 234 is coupled to network 103. Communications subsystem 234 receives information from, and transmits information to network 103. In some embodiments, communications subsystem 234 includes an alerting subsystem to send out alerts based on received inputs, data received from waveform processing subsystem 230-1 to 230-N, data retrieved from database 232.

In some embodiments, the alerts are sent out based on the results of processing performed by waveform processing subsystem 230-1 to 230-N. In some embodiments, this alerting is performed by communications subsystem 234 on its own. In other embodiments, as will be explained below, communications subsystem 234 works with third party systems 108 to perform alerting.

Database 232 stores information and data for use by waveform analysis subsystem 102. This includes, for example, waveforms captured from cuff unit 101, hemodynamic parameters and blood pressure parameters extracted by waveform processing subsystem 230-1 to 230-N, one or more algorithms and programs necessary to perform processing of received data and waveforms, and other test subject data as needed.

In one embodiment, database 232 further comprises a database server. The database server receives one or more commands from, for example, waveform processing subsystem 230-1 to 230-N and communication subsystem 234, and translates these commands into appropriate database language commands to retrieve and store data into database 232. In one embodiment, database 232 is implemented using one or more database languages known to those of skill in the art, including, for example, Structured Query Language (SQL). In a further embodiment, database 232 stores data for a plurality of test subjects. Then, there may be a need to keep the set of data related to each test subject separate from the data relating to the other test subjects. In some embodiments, database 232 is partitioned so that data related to each test subject is separate from the other test subject. Then, within each partition, different groups of people may have access to different subsets of the data set within the partition. For example, a test subject only has access to systolic and diastolic blood pressure data. A practitioner such as a doctor or a nurse or an emergency medical technician has access to a broader subset of data for the test subjects that they are responsible for. A researcher has access to a broader subset of data for an entire population of test subjects. In a further embodiment, when data is entered into database 232, associated metadata is added so as to make it more easily searchable. In a further embodiment, the associated metadata comprises one or more tags. In yet another embodiment, database 232 presents an interface to enable the entering of search queries. Further details of this are explained below.

Waveform processing subsystems 230-1 to 230-N perform processing and analysis within waveform analysis subsystem 102 using one or more algorithms and programs residing on waveform analysis subsystem 102. These algorithms and programs are stored in, for example, database 232 as explained above, or within waveform processing subsystems 230-1 to 230-N.

Examples of processing performed by waveform processing subsystem 230-1 to 230-N include:
Processing of waveforms transmitted from cuff unit 101 or stored on database 232 to extract blood pressure parameters and other hemodynamic parameters;
Analysis and comparison of waveforms across various segments of test subject populations;
Statistical analyses of blood pressure parameters and other hemodynamic parameters as necessary.

In some embodiments, waveform processing subsystems 230-1 to 230-N perform one or more advanced waveform analytics techniques. These one or more advanced waveform analytics techniques will be explained further below. In some embodiments, waveform processing subsystems 230-1 to 230-N perform these advanced waveform analytics techniques on their own. In other embodiments, waveform processing subsystems 230-1 to 230-N perform these advanced waveform analytics techniques together with third party systems 108, as will be explained below.

Interconnection 233 connects the various components of waveform analysis subsystem 102 to each other. In one embodiment, interconnection 233 is implemented using, for example, network technologies known to those in the art. These include, for example, wireless networks, wired networks, Ethernet networks, local area networks, metropolitan area networks and optical networks. In one embodiment, interconnection 233 comprises one or more subnetworks. In another embodiment, interconnection 233 comprises other technologies to connect multiple components to each other including, for example, buses, coaxial cables, USB connections and so on.

Various implementations are possible for waveform analysis subsystem 102 and its components. In one embodiment, waveform analysis subsystem 102 is implemented using a cloud-based approach. In another embodiment, waveform analysis subsystem 102 is implemented across one or more facilities, where each of the components are located in different facilities and interconnection 233 is then a network-based connection. In a further embodiment, waveform analysis subsystem 102 is implemented within a single server or computer. In yet another embodiment, waveform analysis subsystem 102 is implemented in software. In another embodiment, waveform analysis subsystem 102 is implemented using a combination of software and hardware.

By moving the processing functionality to waveform analysis subsystem 102, this increases the processing power, storage capacity and information aggregation capability of system 100.

Communicative coupling so as to allow transmission of data between cuff unit 101 and terminal 104 is achieved via connection 105 as shown in FIG. 1. Connection 105 is achieved using appropriate wired or wireless technologies. Examples of wired technologies include, for example, USB. Examples of wireless technologies include personal area network technologies such as Bluetooth or Zigbee. In one embodiment, connection 105 is implemented using Wi-Fi.

Network 103 may be implemented in a variety of ways. For example, in one embodiment, network 103 comprises one or more subnetworks. In another embodiment, network 103 is implemented using one or more types of networks known to those of skill in the art. These types of networks include, for example, wireless networks, wired networks, Ethernet networks, local area networks, metropolitan area networks and optical networks.

Terminal 104 is for example a tablet, laptop, smartphone, desktop, wearable device or any suitable computing device capable of:
connecting to cuff unit 101 to, for example, receive and transmit data as needed and initiate operation of cuff unit 101 remotely; and
connect to network 103 so as to receive and transmit data as needed.

In one embodiment, terminal 104 has a software program such as an application or "app" installed on it to enable
communication with communications unit 205 on cuff unit 101 to receive and transmit data as necessary,
control of the operation of cuff unit 101 via communications unit 205 on cuff unit 101, and
display of extracted measures and results of analysis transmitted by waveform analysis subsystem 102.

In a further embodiment, the above is performed via an interface comprising a 'dashboard_. In a further embodiment, the app installed on terminal 104 depends on the status of the person using said terminal 104 to perform the test. For example, the installed app depends on whether terminal 104 is being used by a consumer, practitioner or a researcher. Then, the "dashboard" or the interface is customized based on the status and profile of the user of the terminal 104.

In addition to the above, there may be one or more user devices 107 connected to network 103 other than terminal 104. These include, for example,
user devices associated with researchers,
user devices associated with practitioners, or
other user devices belonging to the test subject.
Examples of one or more user devices 107 include, for example, smartphones, laptops, desktops, tablets, wearable devices and other suitable networked devices.

Third party systems 108 are systems outside of the one or more user devices 107 and terminal 104. These include, for example, hospital systems, research institution systems, systems associated with educational institutions, picture archiving and communications systems (PACS), systems associated with clinics, and so on. In some embodiments, third party systems 108 include manufacturer quality control systems looking to access the data to enable calibration and quality control of manufactured blood pressure monitors. In a further embodiment, third party systems 108 also includes, for example, other oscillometric blood pressure equipment seeking to retrieve data for calibration and validation.

Figure 2K:
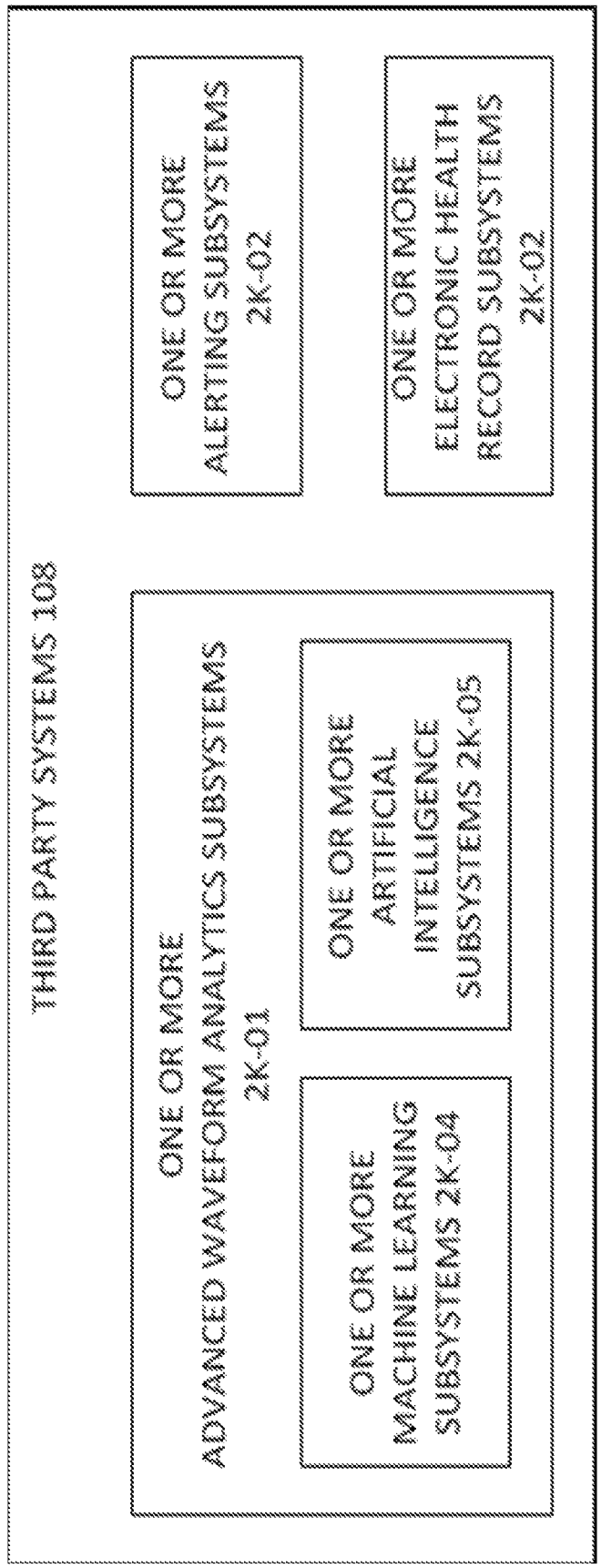
FIG. 2K shows an example embodiment of third party systems.

FIG. 2K shows an example embodiment of third party systems 108. In some embodiments, third party systems 108 comprise one or more advanced waveform analytics subsystems 2K-01, which are designed to perform one or more advanced waveform analytics techniques on the database records stored in database 232. These will be discussed further below. In some embodiments, as explained previously, these one or more advanced waveform analytics subsystems 2K-01 work together with waveform processing subsystems 230-1 to 230-N within waveform analysis subsystem 102 to perform the one or more advanced waveform analytics. In some embodiments, these one or more advanced waveform analytics subsystems 2K-01 perform the one or more advanced waveform analytics on their own.

In some embodiments, the one or more advanced waveform analytics subsystems 2K-01 comprise one or more machine learning (ML) subsystems 2K-04 and one or more artificial intelligence (AI) subsystems 2K-05. As will be explained further below, one or more subsystems 2K-04 and 2K-05 perform the ML and AI techniques which are part of the one or more advanced waveform analytics techniques.

In further embodiments, third party systems 108 send out alerts. In some embodiments, third party systems 108 comprise one or more alerting subsystems 2K-02. In some embodiments these one or more alerting subsystems 2K-02, either together with communication subsystems 234 in waveform analysis subsystem 102 or on their own, work to send out alerts based on at least one of:
- inputs received at waveform analysis subsystem 102, and
- data received from waveform analysis subsystem 102.
  - This includes, for example,
    - data retrieved from database 232, or
    - results of processing obtained from waveform processing subsystems 230-1 to 230-N.

While the above describes a situation where the waveform analysis subsystem 102 performs the processing and calculations as necessary in system 100, one of skill in the art would realize that other embodiments are also possible. In some example embodiments, at least some of the processing in system 100 is performed in one or more of
- terminal 104,
- one or more user devices 107,
- third party systems 108, and
- cuff unit 101.

Figure 3:
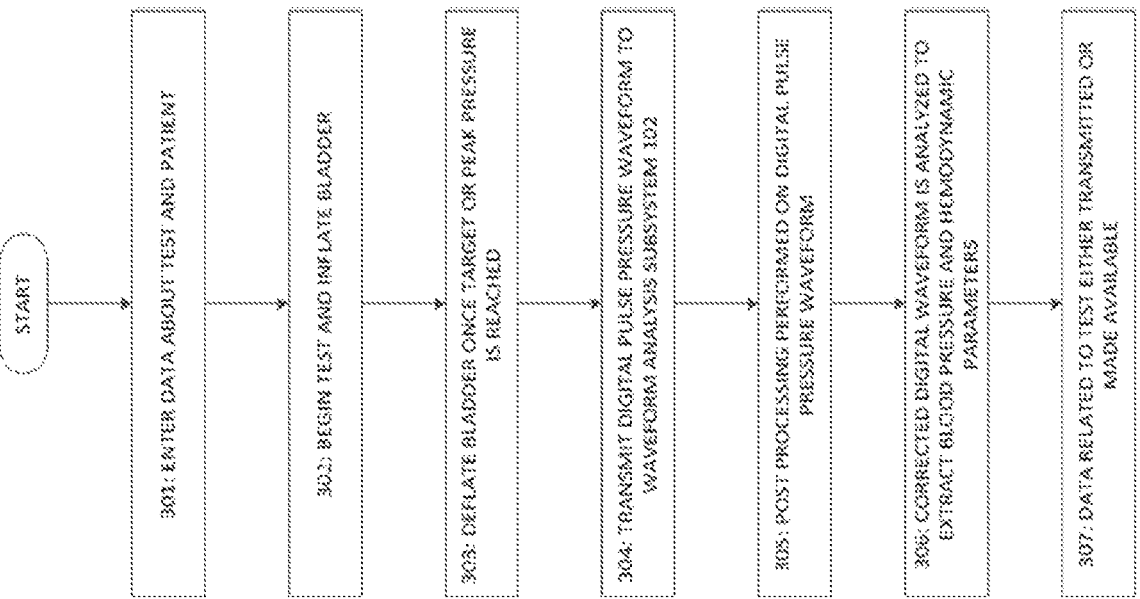
FIG. 3 shows an example embodiment of a process to extract blood pressure and hemodynamic parameters.

FIG. 3 details a flowchart of operation for the wrist-based oscillometric blood pressure measuring system described above.

In step 301, relevant entry and identification data about the test and the test subject is entered by either the test subject or a practitioner at, for example, terminal 104 using the installed app or dashboard. This comprises, for example:
- Name of test subject;
- Name of person performing the test;
- Date and time of test;
- Location of test;
- Test subject identification data such as
  - test subject age,
  - test subject gender,
  - test subject date of birth,
  - test subject race,
  - test subject biometric information such as
    - height,
    - weight, and
    - body mass index (BMI),
  - test subject government health care number, and
  - test subject insurance policy number.
- Other relevant test subject information such as
  - medication taken, and
  - diagnosed conditions.

Steps 302 and 303 represent the testing phase and detail the acquisition of a digital pulse pressure waveform from a wrist of the test subject. In step 302 of FIG. 3, cuff unit 101 is first strapped around a wrist of the test subject. Then as is known to one of skill in the art: As part of the oscillometric technique used by cuff unit 101, bladder 201 is inflated by air pressure control unit 201-1 based on commands sent from measurement unit 202 so as to occlude a radial artery corresponding to the wrist of the test subject on which cuff unit 101 is strapped to. In one embodiment step 302 is initiated from terminal 104 by, for example, the test subject or practitioner by either clicking on a mouse or touching a button on a screen. The resulting analog pulse pressure waveform is captured from the start of the inflation of the bladder 201 by pressure sensor 211 residing within measurement unit 202. As explained previously, this captured analog pulse pressure waveform is then sampled and converted to a digital pulse pressure waveform by A/D converter 213 within measurement unit 202, and temporarily stored within storage 214 before being transmitted to terminal 104 via processor 212 and communications unit 205.

As explained before, A/D converter 213 has a 24-bit or higher conversion resolution. The reason for this is as follows: The range over which the bladder 201 inflates is relatively high. However, the variations in the analog pulse pressure waveform which are captured and used in subsequent analyses and processing are extremely small in comparison to the range. Therefore it is important for the digital pulse pressure waveform to be a high fidelity digital representation of the analog pulse pressure waveform, necessitating a 24-bit or higher conversion resolution for the A/D converter. Having such a high fidelity digital representation increases the accuracy of extraction of blood pressure parameters and other hemodynamic parameters by waveform processing subsystems 230-1 to 230-N. This provides another reason for performing processing at the waveform analysis subsystem 102: High fidelity digital representations typically occupy larger sized files, meaning that processing these files is time, resource and power-consuming. By moving the processing to the waveform analysis subsystem 102 this reduces power consumption and resource usage at the cuff unit 101 or terminal 104. It also enables more powerful processing techniques to be used.

In step 303 of FIG. 3, as known to one of skill in the art: As part of the oscillometric technique, once bladder 201 reaches the peak or target pressure, it is deflated by air pressure control unit 201-1 so as to de-occlude the radial artery. The pressure sensor 211 residing within measurement unit 202 continue to capture the analog pulse pressure waveform until the end of the deflation of the bladder 201. As explained previously, the captured analog pulse pressure waveform is converted to a digital pulse pressure waveform by A/D converter 213 within measurement unit 202 and temporarily stored within storage 214 before transmission to terminal 104 via processor 212 and communications unit 205. In addition to the digital pulse pressure waveform, data from error correction unit 204 is also captured and transmitted to terminal 104 to perform adjusting of the digital pulse pressure waveform.

In step 304 of FIG. 3, the following data sets are transmitted from terminal 104 to waveform analysis subsystem 102 via network 103:
- the digital pulse pressure waveform;
- the relevant entry and identification data; and
- data necessary to perform adjusting of the digital pulse pressure waveform comprising, for example, the data captured by error correction unit 204.

Since these data sets are relatively large and very complex, moving the processing including the adjusting of the digital pulse pressure waveform and analysis to the waveform analysis subsystem 102 enables the application of more powerful processors to these large and very complex data sets than would be available in terminal 104 or cuff unit 101. Furthermore, moving the processing to the waveform analysis subsystem 102 reduces the power consumption of terminal 104 and cuff unit 101.

In a further embodiment, as part of step 304, prior to transmission of the data, the data sets are de-identified so as to ensure compliance with regulations such as the United States (US) Health Insurance Portability and Accountability Act (HIPAA) or European Union (EU) regulations.

In a further embodiment, so as to ensure security and privacy, the data sets are encrypted. In a further embodiment, the data sets are compressed so as to reduce bandwidth usage over network 103.

Steps 305 and 306 provide details of the processing performed on the acquired digital pulse pressure waveform. In step 305, if the transmitted data sets have been compressed and/or encrypted, the data sets are first decompressed and/or decrypted. Then the digital pulse pressure waveform is stored on database 232. In one embodiment, digital pulse pressure waveform metadata associated with the digital pulse pressure waveform is created and stored in database 232. Then, the digital pulse pressure waveform metadata is created based on, for example:

Entry and identification data entered in step 301; and

The transmitted data necessary to perform post-processing.

In one embodiment, the digital pulse pressure waveform metadata comprises, for example, the creation of one or more digital pulse pressure waveform tags so as to enable searchability of the waveform.

Among other reasons, the digital pulse pressure waveform and associated metadata is stored in order to enable forward compatibility with future hardware and also for improved usability. Storing of the associated metadata also enables and improves the searchability of the waveforms stored within database 232.

Then also as part of step 305, the digital pulse pressure waveform is then adjusted by the one or more of waveform processing subsystems 230-1 to 230-N so as to improve the accuracy of subsequent analyses. In one embodiment, one of the adjusting operations involves using the transmitted readings from the error correction unit 204 to detect at least one of test subject movement and incorrect limb positioning. Then, another adjusting operation involves correcting the digital pulse pressure waveform for the detected at least one of movement and incorrect limb positioning. The corrected digital pulse pressure waveform is then stored on database 232. In one embodiment, as part of this step, an error code is returned to the terminal 104, depending on the processing of the data transmitted from the error correction unit 204. In one embodiment, a 'no error_ code is returned indicating that one or more waveform processing subsystems 230-1 to 230-N has determined that digital pulse pressure waveform represents a complete reading and has been mathematically checked to be correct. In a further embodiment, one or more waveform processing subsystems 230-1 to 230-N determines the magnitude of the error in at least one of incorrect limb positioning and limb movement based on the one or more readings transmitted from the error correction unit 204. If the magnitude of the error is sufficiently small such that digital pulse pressure waveform can be corrected by waveform processing subsystems 230-1 to 230-N, then after the correction is performed a 'no error_ code is returned. In one embodiment, if the one or more waveform processing subsystems 230-1 to 230-N determines that the magnitude of the error is too large, then the processing is stopped. This could occur if, for example, the test subject was detected to have moved too much or the deviation of the limb positioning from the ideal position is too large. Then an 'error_ or 'invalid reading_ code is returned. In one embodiment, to determine whether the magnitude is sufficiently small or too large is performed by comparing the magnitude to one or more error correction thresholds. These one or more error correction thresholds are determined based on, for example, known correction parameters and/or correction capabilities of the waveform processing subsystems 230-1 to 230-N. The codes mentioned above are returned to, for example, terminal 104 via network 103. In additional embodiments, these codes are also transmitted to at least one of third party systems 108 and one or more user devices 107. In a further embodiment, the corrected digital pulse pressure waveform is associated with the digital pulse pressure waveform metadata, so as to, for example, enable searching and retrieval. In a further embodiment, the digital pulse pressure waveform metadata is updated to reflect the results of the adjusting and record any codes that were returned along with data surrounding any codes that were returned such as transmission time and records of receipt of the transmitted codes.

In step 306 of FIG. 3, the corrected digital pulse pressure waveform is retrieved from database 232 and analyzed by, for example, one or more of waveform processing subsystems 230-1 to 230-N within waveform analysis subsystem 102. In one embodiment, the corrected digital pulse pressure waveform is converted to a radial arterial waveform. Then measures such as blood pressure and other hemodynamic parameters known to those of skill in the art are extracted. These measures comprise, for example:

Systolic Blood pressure (in units of mmHg),
Systolic Blood Pressure Confidence Interval (in units of mmHg),
Systolic Blood Pressure Confidence Level (%),
Mean Arterial Blood Pressure (MABP) (in units of mmHg),
MABP Confidence Interval (in units of mmHg),
MABP Confidence Level (%),
Diastolic Blood Pressure (in units of mmHg),
Diastolic Blood Pressure Confidence Interval (in units of mmHg),
Diastolic Blood Pressure Confidence Level (%),
Pulse Rate (beats per minute or pulses per minute),
Pulse Rate Variability (either in % or beats per minute or pulses per minute),
Radial Arterial Pulse Rise Time (in seconds),
Radial Arterial Pulse Rise Time Confidence Interval (in seconds),
Radial Arterial Pulse Peak Time (in seconds),
Radial Arterial Pulse Peak Time Confidence Interval (in seconds),
Radial Arterial Pulse Fall Time (in seconds),
Radial Arterial Pulse Fall Time Confidence Interval (in seconds),
Pulse Pressure (in units of mmHg),
Radial augmentation index (RAI) (%),
Ejection Duration or Ejection Time (in seconds),
Radial Augmentation Pressure (in units of mmHg),
Central Aortic Systolic Pressure (CASP),
Peak Relative Time (in seconds),
Ejection Duration Index (%),
Breathing Rate,
Fibrillation,
Tachycardia,
Missed Beats,
Pulsus alternans,
Premature Contractions,
Circadian,
Hemodynamic BMI,
Hemodynamic Age,
Hemodynamic Diagnosis,
Hemodynamic Reactions, and
Breathing Rate Confidence Interval.

Extraction of this amount of parameters is not performed in prior art wrist-based cuff systems, and is made possible by the improved accuracy of processing due to the high fidelity digital pulse pressure waveform provided by the 24-bit or higher resolution A/D converter. In particular, the following parameters were not extracted in prior art wrist-based cuff systems, but are extracted in this system due to the capability of the 24-bit or higher resolution A/D converter to capture a high fidelity digital pulse pressure waveform:

Radial Arterial Pulse Rise Time (in seconds),
Radial Arterial Pulse Rise Time Confidence Interval (in seconds),
Radial Arterial Pulse Peak Time (in seconds),
Radial Arterial Pulse Peak Time Confidence Interval (in seconds),
Radial Arterial Pulse Fall Time (in seconds),
Radial Arterial Pulse Fall Time Confidence Interval (in seconds),
Pulse Pressure (in units of mmHg),
Radial augmentation index (RAI) (%),
Ejection Duration or Ejection Time (in seconds),
Radial Augmentation Pressure (in units of mmHg),
Central Aortic Systolic Pressure (CASP),
Peak Relative Time (in seconds),
Ejection Duration Index (%),
Breathing Rate,
Fibrillation,
Tachycardia,
Missed Beats,
Pulsus alternans,
Premature Contractions,
Circadian,
Hemodynamic BMI,
Hemodynamic Age,
Hemodynamic Diagnosis,
Hemodynamic Reactions,
Breathing Rate Confidence Interval.

The combination of the 24-bit or higher resolution A/D converter 213, the modular design, and coupling the waveform analysis subsystem 102 to the cuff unit via a network such as network 103, enables a portable cuff unit that is able to capture high fidelity digital pulse pressure waveforms, and
process these captured high fidelity digital pulse pressure waveforms using powerful processing techniques.

Additionally, since the acquired digital pulse pressure waveforms are substantially invariant over the 360 degree range of angles of rotation during attachment to the wrist, then the extracted values of at least some of these parameters are also substantially invariant over the 360 degree range of angles of rotation.

Some of the hemodynamic parameters mentioned above are anomalies. These include, for example, tachycardia, missed beats and fibrillation. In some embodiments, as will be explained in more detail below, specialized anomaly detection techniques are used as part of step 306 to detect some of these anomalies. These are performed by, for example, at least one of waveform processing subsystems 230-1 to 230-N within waveform analysis subsystem 102 or by third party systems 108.

As part of step 306, the radial arterial waveforms and the extracted measures are stored on database 232. In a further embodiment, the radial arterial waveforms and the extracted measures are associated with the digital pulse pressure waveform metadata, so as to, for example, enable searching and retrieval. In a further embodiment, the digital pulse pressure waveform metadata is updated to reflect conversion of the corrected digital pulse pressure waveform to a radial arterial waveform, and the extraction of the measures.

In step 307, in one embodiment, once the blood pressure parameters and hemodynamic parameter extraction is completed, at least one of the following data sets is transmitted or made available to terminal 104 to be viewed or searched by the test subject and/or the practitioner:

The corrected digital pulse pressure waveform,
The radial arterial waveform,
At least one of the extracted blood pressure and hemodynamic parameters, and
The digital pulse pressure waveform metadata.

In some additional embodiments, these data sets are transmitted to or made available for searching or viewing to third party systems 108 and one or more user devices 107.

There may also be functionalities to send out one or more alerts based on certain events using a messaging technique such as email, voicemail, instant messaging, Short Message Service (SMS), telephone call and so on. These one or more alerts are sent out by, for example, communications subsystem 234 of waveform analysis subsystem 102 as shown in FIG. 2J; or one or more of third party systems 108.

In some embodiments, these one or more alerts are sent out as part of step 307. In other embodiments, these one or more alerts are sent out at conclusion of, for example, earlier steps in the process such as step 305 or step 306.

Examples of events for which alerts are sent out include:
conclusion of, for example, earlier steps in the process such as step 305 or step 306
abnormal blood pressure or hemodynamic parameter readings based on the analysis performed in step 306; or
anomalies such as tachycardia, missed beats or fibrillation.

As would be known to one of skill in the art, variations on the process described in FIG. 3 above are also possible. As explained previously, in some embodiments, cuff unit 101 is coupled to waveform analysis subsystem 102 via network 103 without coupling to terminal 104. In these embodiments, in steps 302 and 303, the digital pulse pressure waveform is directly transmitted to waveform analysis subsystem 102 instead of terminal 104. Step 304 is then not performed.

Other variations are also possible. While the above describes embodiments where the one or more algorithms or programs which perform processing and analysis reside in waveform analysis subsystem 102, other embodiments are also possible.

In one embodiment, at least some of the processing and analysis detailed in steps 305 and 306 is performed within at least one of:
terminal 104,
one or more user devices 107,
third party systems 108, and
cuff unit 101.

In a specific embodiment, at least some of the one or more algorithms and programs are stored either temporarily or permanently in at least one of terminal 104 and cuff unit 101. Then, at least some of the processing and analysis detailed in steps 305 and 306 is performed within at least one of terminal 104 and cuff unit 101. The remainder, if any, of the processing takes place in waveform analysis subsystem 102. The captured data used for the processing and analysis such as the digital pulse pressure waveforms are then transmitted at a later time or deleted. This is useful if, for example, at least one of connections 105 and 106 are either down or are intermittent.

In these embodiments where at least some of the processing in steps 305 and 306 are performed by components other than waveform analysis subsystem 102, then these other components perform alerting as explained previously. For example, a third party system 108 sends out an alert when an abnormal blood pressure or hemodynamic parameter value or an anomaly is detected.

FIG. 3 illustrates the process flow for a single test subject. In one embodiment, the process flow outlined in FIG. 3 is repeated for a plurality of test subjects, and a database record comprising at least one of
- digital pulse pressure waveforms,
- corrected digital pulse pressure waveform,
- radial arterial waveforms,
- extracted blood pressure parameters and hemodynamic parameters, and
- digital pulse pressure waveform metadata corresponding to each test subject is created and stored in database 232 of waveform analysis subsystem 102. In some embodiments, as will be explained further below, having a comprehensive database record corresponding to each of the plurality of test subjects enables performance of certain advanced waveform analytics.

As explained previously, using metadata enables enhanced searchability of this data using a search query. In an embodiment, a search query is created to retrieve data from, for example, database 232 corresponding to a segment of the plurality of test subjects which meets the parameters of the search query. The parameters of the search query include, for example:
- age,
- gender,
- race,
- medical condition,
- date of test,
- medications taken,
- time of test, and
- location of facility where the test was taken.

In a further embodiment, the process flow illustrated in FIG. 3 is repeated for a test subject across a period of time. In an embodiment, the radial arterial waveforms and extracted parameters corresponding to each repetition are analyzed and compared to each other to understand how the test subject has changed physiologically over a period of time. This period of time could correspond to, for example, the length of any type of intervention, lifestyle, diet and condition that affects a test subject's hemodynamics. In one embodiment, as will be explained further below, advanced waveform analytics techniques are used to perform these studies.

In a further embodiment, the process flow illustrated in FIG. 3 is performed at a scheduled time. For example, terminal 104 or cuff unit 101 has a real time clock which uses an alarm to notify either the test subject or another person to perform the process flow illustrated in FIG. 3 at a scheduled time. In a further embodiment, this alarm is set up so as to repeat periodically, for example, either daily, weekly or hourly.

In a further embodiment, the process flow illustrated in FIG. 3 is performed automatically. Then, for example, terminal 104 or cuff unit 101 has a real time clock, which wakes up at one or more scheduled times and automatically performs a reading. This automatic blood pressure monitoring functionality is useful in, for example, non-ambulatory applications and performing sleep studies. In a further embodiment, the one or more scheduled times are programmed remotely by, for example, a practitioner using terminal 104, or one or more user devices 107 or third party systems 108.

In a further embodiment, different subsets of information are either transmitted or made available for viewing to different groups of people depending on their status. For example, as explained above, in step 307 of FIG. 3 the system either transmits or makes available at least one of:
- the corrected digital pulse pressure waveform,
- the radial arterial waveform, and
- at least one of the extracted blood pressure and hemodynamic parameters.

A home-based consumer is likely to be interested only in a narrow subset of the information such as systolic blood pressure, diastolic blood pressure and pulse rate at that time, and how these have varied over a period of time. A practitioner may require a broader subset of information for a given test subject. A researcher may require a much broader subset of the information and not just for one test subject, but for multiple test subjects. In one embodiment, based on a submitted profile or status from, for example, terminal 104 or one or more user devices 107, different subsets are then made available.

In a further embodiment, these subsets are presented via dashboards customized to each group of people. For example, as explained previously, in one embodiment, the app installed on terminal 104 of FIG. 1 depends on the profile or status of the person using terminal 104. So, for example, a consumer dashboard would allow a consumer such as a home-based consumer to visualize the systolic blood pressure, diastolic blood pressure and pulse rate and how this has varied with, for example, BMI or weight or over time. A practitioner dashboard would allow a practitioner to visualize these different measures over time and during, for example, treatment for a given condition, or enable comparisons before and after an event such as a heart attack or a stroke. A researcher dashboard would allow a researcher access to multiple measures for multiple test subjects over a period of time and would also allow, for example, a researcher to perform segmentations as described above.

In further embodiments, these subsets are presented via applications or 'apps_ customized to each group of people. So, in example embodiments where the test subject is a home-based consumer, the test subject will use a consumer dashboard on a consumer app running on a smartphone, tablet or laptop to visualize the subset of information that he or she is likely to be interested in. Similarly, a practitioner or a researcher uses either a practitioner or researcher dashboard on a practitioner or researcher app running on a smartphone, tablet or laptop to visualize the subset of information that he or she is likely to be interested in.

It is recommended that manufacturers of oscillometric blood pressure equipment test algorithmic functions of such equipment using real physiological data as explained in Jilek, J., and M. Stork. "Oscillometric pressure pulse waveforms: their current and prospective applications in biomedical instrumentation." Proceedings of the 13th WSEAS International Conference on Systems, Rodos, Greece. Vol. 2325. 2009. Since database 232 contains real data related to a plurality of test subjects: In one embodiment, a manufacturer which has a system that is part of third party systems 108 in FIG. 1 connects to database 232 via network 103 to test its blood pressure equipment. In addition, in some embodiments, oscillometric blood pressure equipment which is part of third party systems 108 have test interfaces which connect to database 232 via network 103 for validation and calibration. This reduces the costs of testing, development and quality control of oscillometric blood pressure equipment.

Since database 232 contains digital pulse pressure waveforms which are high fidelity digital representations of analog pulse pressure waveforms, these are ideal datasets for future research and testing of, for example, new algorithms and proposed new blood pressure and hemodynamic parameters. In another embodiment, research and development systems which are part of third party systems 108 in FIG. 1 connect to database 232 via network 103 in order to perform searches and retrieve data necessary for testing and research.

As was explained previously, in some embodiments, a comprehensive database record corresponding to each of a plurality of test subjects is stored in database 232. In further embodiments, as mentioned above, one or more advanced waveform analytics techniques are performed on these database records or on data received from cuff unit 101. In some embodiments, these are performed as part of, for example, step 306 of FIG. 3. In other embodiments, these are performed outside of the process flow detailed in FIG. 3. As explained previously, these one or more advanced waveform analytics techniques are performed by, for example, at least one of waveform processing subsystems 230-1 to 230-N within waveform analysis subsystem 102 and third party systems 108, for example by one or more advanced waveform analytics subsystems 2K-01 within third party systems 108.

In some embodiments, these one or more advanced waveform analytics include techniques for performing anomaly detection.

In further embodiments, these one or more advanced waveform analytics techniques comprise using at least one AI or one ML approach. Examples of such techniques are given in, for example, "Machine learning techniques for arterial pressure waveform analysis" by Almeida, Vania G., Joao Vieira, Pedro Santos, Tânia Pereira, H. Pereira, Carlos Correia, Mariano Pego, and Joao Cardoso. Journal of personalized medicine 3, no. 2 (2013): pp. 82-101. As explained above, in some embodiments, these are performed by third party systems 108. In further embodiments, these are performed by, for example, one or more machine learning subsystems 2K-04 or one or more artificial intelligence subsystems 2K-05 within third party systems 108.

In yet other embodiments, these one or more advanced waveform analytics comprise using at least one correlation-based classification technique. This involves, for example, comparing one portion of a database record to
 a different portion of the same database record; or
 a portion of a different database record;
 to determine the degree of correlation between the two portions, and then performing a classification based on this correlation.

In order to accurately perform correlation-based classification, it is necessary to capture high fidelity digital pulse pressure waveforms. The 24-bit or higher resolution of the A/D converter enables capture of high fidelity digital pulse pressure waveforms and therefore improves the accuracy of correlation-based classification.

In some embodiments, correlation-based classification is used to perform clustering.

In some embodiments, correlation-based classification comprises using at least one extra-subject correlation-based classification technique. This is where a portion of a database record belonging to a first subject is compared to one or more portions of database records corresponding to one or more different subjects to determine the degrees of correlations. In some embodiments, this is performed as part of a cluster analysis or clustering. Then, once a group or a cluster is identified comprising one or more subjects which have a high degree of correlation with each other, common characteristics are identified for the group or cluster. Examples of characteristics include:
 International Classification of Disease (ICD) codes,
 age,
 height,
 weight,
 blood pressure, and
 heart rate.

In some embodiments, this comprises performing correlations between the radial arterial waveforms corresponding to each of the subjects.

In some embodiments, these one or more advanced waveform analytics comprises using at least one intra-subject correlation-based classification technique. This is where a portion of a database record belonging to a first subject is compared to one or more different portions of the same database record corresponding to the first subject. In some embodiments, when the presence of significant changes is detected within the first subject, a further determination is made as to whether these changes are positive or negative with respect to the health of the first subject. In further embodiments, the presence of significant changes is detected based on the degree of correlation.

In some embodiments, these one or more advanced waveform analytics comprise performing mitigation and reaction analysis. This comprises, for example,
 determining how a subject is reacting to a particular course of treatment, or
 determining how subjects˜ bodies are reacting to a particular drug within a drug trial.
 This is particularly useful in, for example, research and development of new treatment methods or testing of new drugs, or determining the effectiveness of existing drugs in a particular subject.

Although the algorithms described above including those with reference to the foregoing flow charts have been described separately, it should be understood that any two or more of the algorithms disclosed herein can be combined in any combination. Any of the methods, algorithms, implementations, or procedures described herein can include machine-readable instructions for execution by: (a) a processor, (b) a controller, and/or (c) any other suitable processing device. Any algorithm, software, or method disclosed herein can be embodied in software stored on a non-transitory tangible medium such as, for example, a flash memory, a CD-ROM, a floppy disk, a hard drive, a digital versatile disk (DVD), or other memory devices, but persons of ordinary skill in the art will readily appreciate that the entire algorithm and/or parts thereof could alternatively be executed by a device other than a controller and/or embodied in firmware or dedicated hardware in a well known manner (e.g., it may be implemented by an application specific integrated circuit (ASIC), a programmable logic device (PLD), a field programmable logic device (FPLD), discrete logic, etc.). Also, some or all of the machine-readable instructions represented in any flowchart depicted herein can be implemented manually as opposed to automatically by a controller, processor, or similar computing device or machine. Further, although specific algorithms are described with reference to flowcharts depicted herein, persons of ordinary skill in the art will readily appreciate that many other methods of implementing the example machine readable instructions may alternatively be used. For example, the order of execution of the blocks may be changed, and/or some of the blocks described may be changed, eliminated, or combined.

It should be noted that the algorithms illustrated and discussed herein as having various modules which perform particular functions and interact with one another. It should be understood that these modules are merely segregated based on their function for the sake of description and represent computer hardware and/or executable software code which is stored on a computer-readable medium for execution on appropriate computing hardware. The various functions of the different modules and units can be combined or segregated as hardware and/or software stored on a non-transitory computer-readable medium as above as modules in any manner, and can be used separately or in combination.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of an invention as defined in the appended claims.

What is claimed is:

1. A system for measurement and analysis of blood pressure of a test subject comprising a blood pressure measuring cuff unit, communicatively coupled to a network, comprising:
    an inner layer constructed using a high elasticity material, the inner layer configured to be in contact with a wrist of the test subject;
    an outer layer constructed using a low elasticity material;
    a bladder enclosed between the inner layer and the outer layer, such that the inner layer expands and the outer layer maintains a stable form responsive to inflation of the bladder to contain pressure applied to the wrist, wherein the bladder wraps around the wrist of the test subject and the pressure is applied uniformly to the wrist of the test subject regardless of an angle of rotation of the blood measuring cuff unit when attached to the wrist and a shape of the wrist;
    a plurality of modules, the plurality of modules comprising three or more modules arranged adjacent to each other, such that a first module is connected to a second module by at least one hinge and the second module is connected to a third module by at least one hinge to enable the blood pressure measuring cuff unit to wrap around the wrist;
    one or more components, wherein at least some of the one or more components reside within at least one module of the plurality of modules; and
    a waveform analysis subsystem comprising a communications subsystem coupled to one or more waveform processing subsystems via a first one or more interconnections, wherein the communications subsystem is communicatively coupled to the network; and
    wherein
        the blood pressure measuring cuff unit acquires a digital pulse pressure waveform from the wrist of the test subject, wherein
            the acquisition comprises occlusion and de-occlusion of an artery within the wrist of the test subject,
            the cuff unit transmits the digital pulse pressure waveform to the waveform analysis subsystem via the network,
            the communications subsystem receives the digital pulse pressure waveform from the network,
            the communications subsystem transmits the received digital pulse pressure waveform via the first one or more interconnections to the one or more waveform processing subsystems, and
        the one or more waveform processing subsystems process the digital pulse pressure waveform to extract one or more blood pressure parameters and hemodynamic parameters.

2. The system of claim 1, wherein
the bladder is configured to conform to a shape of the wrist of the test subject, wherein the occlusion of the artery is performed by inflating the bladder and the de-occlusion of the artery is performed by deflating the bladder.

3. The system of claim 1, wherein:
the cuff unit comprises a 3-axis accelerometer;
further wherein
    the 3-axis accelerometer obtains one or more readings,
    the cuff unit transmits the one or more readings to the waveform analysis subsystem over the network,
    the communications subsystem receives the one or more readings from the network,
    the communications subsystem transmits the received one or more readings via the first one or more interconnections to the one or more waveform processing subsystems, and
    the processing of the acquired digital pulse pressure waveform comprises the one or more waveform processing subsystems using the one or more readings to produce a corrected digital pulse pressure waveform, and
    the extraction of one or more blood pressure parameters and hemodynamic parameters is performed using the corrected digital pulse pressure waveform.

4. The system of claim 1, wherein the one or more blood pressure parameters and hemodynamic parameters comprise:
systolic blood pressure,
systolic blood pressure confidence level,
Mean Arterial Blood Pressure (MABP),
MABP confidence interval,
MABP confidence level,
diastolic blood pressure,
diastolic blood pressure confidence interval,
diastolic blood pressure confidence level,
pulse rate,
pulse rate variability,
radial arterial pulse rise time,
radial arterial pulse rise time confidence interval,
radial arterial pulse peak time,
radial arterial pulse peak time confidence interval,
radial arterial pulse fall time,
radial arterial pulse fall time confidence interval,
pulse pressure,
radial augmentation index (RAI),
ejection duration,
radial augmentation pressure,
central aortic systolic pressure (CASP),
peak relative time,
ejection duration index,
breathing rate,
hemodynamic age, and
breathing rate confidence interval.

5. The system of claim 1, wherein:
the cuff unit comprises a measurement subsystem and an analog-to-digital (A/D) converter having a 24-bit or higher resolution;
the acquisition of the digital pulse pressure waveform by the cuff unit comprises the measurement unit capturing an analog pulse pressure waveform, the A/D converter sampling the captured analog pulse pressure waveform, the A/D converter converting the sampled analog pulse pressure waveform into the digital pulse pressure waveform, and the 24-bit or higher resolution of the A/D converter causes the digital pulse pressure waveform to be a high fidelity digital representation of the analog pulse pressure waveform;

the high fidelity digital representation is operative to cause an increase in an accuracy of the extraction of said one or more blood pressure parameters and hemodynamic parameters; and one or more waveform analytics are performed on the digital pulse pressure waveform by at least one of the one or more waveform processing subsystems or a third party system, wherein the one or more waveform analytics comprise using at least one correlation-based classification technique, and the high fidelity digital representation is operative to cause an increase in an accuracy of the at least one correlation-based classification technique.

6. The system of claim 1 wherein the first module comprises a first part of the at least-_some of the one or more components, the second module comprises a second part of the at least some of the one or more components, the first part and the second part are electrically coupled by a second one or more interconnections;

the construction of the outer layer using the low elasticity material enables the second one or more interconnections to be preserved during the inflating and deflating of the bladder.

7. The system of claim 1, wherein the first module comprises a first part of the at least some of the one or more components, the second module comprises a second part of the at least some of the one or more components, the at least one hinge comprising a first hinge, the first part and the second part are electrically coupled by a second one or more interconnections, further wherein at least one of the second one or more interconnections occurs via the first hinge.

8. The system of claim 1, wherein the some of the one or more components residing within the plurality of modules are distributed among the plurality of modules to reduce a thickness of the cuff unit.

9. The system of claim 8, wherein a size of each module of the plurality of modules is selected to enable accommodation of at least one part of the at least some of the one or more components, and to enable the wrapping to conform to a shape of the wrist of the test subject.

10. The system of claim 1, wherein the one or more waveform processing subsystems process the digital pulse pressure waveform to either detect or perform one or more of tachycardia,
missed beats,
pulsus alternans,
premature contractions,
circadian events,
hemodynamic age,
hemodynamic diagnosis, and
hemodynamic reactions.

11. A system for measurement and analysis of blood pressure of a test subject comprising a blood pressure measuring cuff unit, wherein
the cuff unit comprises:
an inner layer constructed using a high elasticity material, the inner layer configured to be in contact with a wrist of the test subject;
an outer layer constructed using a low elasticity material;
a bladder enclosed between the inner layer and the outer layer, such that the inner layer expands and the outer layer maintains a stable form responsive to inflation of the bladder to contain pressure applied to the wrist, wherein the bladder wraps around the wrist of the test subject and the pressure is applied uniformly to the wrist of the test subject regardless of an angle of rotation of the blood measuring cuff unit when attached to the wrist and a shape of the wrist;
the cuff unit is constructed using a plurality of modules, wherein
each of the plurality of modules comprises a physical enclosure,
at least some of the one or more components reside within at least one of the physical enclosures corresponding to at least one of the plurality of modules,
each of the plurality of modules are arranged adjacent to each other, further wherein
a first module of the plurality of modules is connected to a second module of the plurality of the modules adjacent to the first module by at least one hinge, and
the cuff unit coupled to a network;
a waveform analysis subsystem comprising a communications subsystem coupled to one or more waveform processing subsystems via a first one or more interconnections,
wherein the communications subsystem is coupled to the network; and
wherein
the cuff unit acquires a digital pulse pressure waveform from the wrist of the test subject, further wherein
the acquisition comprises occlusion and de-occlusion of an artery within the wrist of the test subject,
the cuff unit transmits the digital pulse pressure waveform to the waveform analysis subsystem via the network,
the communications subsystem receives the digital pulse pressure waveform from the network, and transmits the received digital pulse pressure waveform via the first one or more interconnections to the one or more waveform processing subsystems, and
the one or more waveform processing subsystems process the digital pulse pressure waveform to extract one or more blood pressure parameters and hemodynamic parameters.

12. The system of claim 11, wherein the one or more waveform processing subsystems process the digital pulse pressure waveform to either detect or perform one or more of tachycardia,
missed beats,
pulsus alternans,
premature contractions,
circadian events,
hemodynamic age, hemodynamic diagnosis, and
hemodynamic reactions.

13. The system of claim 11, wherein the one or more blood pressure parameters and hemodynamic parameters comprise:
systolic blood pressure,
systolic blood pressure confidence level,
Mean Arterial Blood Pressure (MABP),
MABP confidence interval,
MABP confidence level,
diastolic blood pressure,
diastolic blood pressure confidence interval,
diastolic blood pressure confidence level,
pulse rate,
pulse rate variability,
radial arterial pulse rise time,
radial arterial pulse rise time confidence interval,
radial arterial pulse peak time,
radial arterial pulse peak time confidence interval,
radial arterial pulse fall time confidence interval,
pulse pressure,
radial augmentation index (RAI),
ejection duration,
radial augmentation pressure,
central aortic systolic pressure (CASP),
peak relative time,
ejection duration index,
breathing rate,
hemodynamic age, and
breathing rate confidence interval.

14. The system of claim 11, wherein
the first module comprises a first part of the some of the one or more components;
the second module comprises a second part of the some of the one or more components;
the at least one hinge comprising a first hinge; and
the first part and the second part are electrically coupled by a second one or more interconnections, wherein at least one of the second one or more interconnections occurs via the first hinge.

* * * * *